(12) United States Patent
Ma et al.

(10) Patent No.: US 11,896,407 B2
(45) Date of Patent: Feb. 13, 2024

(54) MEDICAL IMAGING BASED ON CALIBRATED POST CONTRAST TIMING

(71) Applicant: The Trustees of Columbia University in the City of New York, New York, NY (US)

(72) Inventors: Jingchen Ma, New Haven, CT (US); Laurent Dercle, New York, NY (US); Binsheng Zhao, Forest Hills, NY (US); Lin Lu, New York, NY (US); Lawrence H. Schwartz, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 373 days.

(21) Appl. No.: 17/303,145

(22) Filed: May 21, 2021

(65) Prior Publication Data
US 2021/0279868 A1 Sep. 9, 2021

Related U.S. Application Data

(63) Continuation of application No. PCT/US2019/062552, filed on Nov. 21, 2019.
(Continued)

(51) Int. Cl.
*G06K 9/00* (2022.01)
*A61B 6/03* (2006.01)
(Continued)

(52) U.S. Cl.
CPC .............. *A61B 6/032* (2013.01); *G06N 3/08* (2013.01); *G06T 7/0012* (2013.01);
(Continued)

(58) Field of Classification Search
CPC ......... A61B 6/032; A61B 6/481; A61B 5/055; G06N 3/08; G06T 7/0012;
(Continued)

(56) References Cited

U.S. PATENT DOCUMENTS

| | | |
|---|---|---|
| 2009/0080743 A1 | 3/2009 | Launay et al. |
| 2009/0105582 A1 | 4/2009 | Dougherty et al. |

(Continued)

OTHER PUBLICATIONS

International Preliminary Report on Patentability received for PCT Patent Application No. PCT/US2019/062552, dated Jun. 3, 2021, 11 pages.
(Continued)

*Primary Examiner* — Dhaval V Patel
(74) *Attorney, Agent, or Firm* — Wolter Van Dyke Davis, PLLC; Eugene J. Molinelli; Timothy H. Van Dyke

(57) ABSTRACT

Techniques measuring post contrast phase include collecting 3D medical imagery of a subject after injection with a contrast agent. A first set of slices is obtained in which each includes a first anatomical feature selected from a portal vein, aorta, inferior vena cava, liver, spleen or renal cortex. A second set of slices is obtained in which each includes a different second anatomical feature. A first image region is obtained from the first set and a different second image region from the second set. A trained convolutional neural network is configured to input the first image region to a first plurality of convolutional hidden layers and the second image region to a second plurality of convolutional hidden layers and output from both to a fully connected hidden layer that outputs a post contrast phase. Output data is presented based on the post contrast phase.

22 Claims, 11 Drawing Sheets

FIG. 1C

Related U.S. Application Data

(60) Provisional application No. 62/771,604, filed on Nov. 27, 2018, provisional application No. 62/770,390, filed on Nov. 21, 2018.

(51) Int. Cl.
   *G06N 3/08* (2023.01)
   *G06T 7/00* (2017.01)

(52) U.S. Cl.
   CPC .............. *G06T 2207/10081* (2013.01); *G06T 2207/20081* (2013.01); *G06T 2207/20084* (2013.01); *G06T 2207/30056* (2013.01); *G06T 2207/30096* (2013.01); *G06T 2207/30101* (2013.01)

(58) Field of Classification Search
   CPC . G06T 2207/10081; G06T 2207/20081; G06T 2207/20084; G06T 2207/30056; G06T 2207/30096; G06T 2207/30101; G06T 11/008; G01R 33/5601; G01R 33/5608; G01R 33/5635
   See application file for complete search history.

(56) References Cited

U.S. PATENT DOCUMENTS

| | | |
|---|---|---|
| 2013/0265046 A1 | 10/2013 | Koch |
| 2017/0186195 A1 | 6/2017 | Lin et al. |
| 2017/0330029 A1 | 11/2017 | Turcot et al. |

OTHER PUBLICATIONS

International Search Report and Written Opinion received for PCT Patent Application No. PCT/US2019/062552, dated Feb. 11, 2020, 11 pages.

Milenkovic, J., et al., "Characterization of spatiotemporal changes for the classification of dynamic contrast-enhanced magnetic-resonance breast lesions." In: Artificial intelligence in medicine, vol. 59, Issue 2, Jun. 2013, pp. 101-114.

MEDICAL IMAGING BASED ON CALIBRATED POST CONTRAST TIMING

CROSS-REFERENCE TO RELATED APPLICATIONS

This application is a continuation of PCT Appln. No. PCT/US19/62552 filed Nov. 21, 2019 which claims benefit of Provisional Appln. 62/770,390, filed Nov. 21, 2018, and Provisional Appln. 62/771,604, filed Nov. 27, 2018, the entire contents of each of which are hereby incorporated by reference as if fully set forth herein, under 35 U.S.C. § 119(e).

STATEMENT OF GOVERNMENTAL INTEREST

This invention was made with government support under Contract No. CA140207 awarded by the National Institutes of Health. The government has certain rights in the invention.

BACKGROUND

Cross sectional imaging is an imaging technique which produces a large series of two-dimensional (2D) images of a subject, e.g., a human subject. Examples of cross-sectional imaging techniques include computerized tomography (CT), magnetic resonance imaging (MRI), positron emission tomography (PET), SPECT scanning, ultrasonography (US), among others. A set of cross sectional images for a single patient, e.g., for different axially located cross-sections or for the same cross section at different times can be considered three dimensional (3D) image data, and even four dimensional (4D) image data for combinations of axial and temporal cross sectional images.

Various analytical approaches can be applied to the cross-sectional images to detect and highlight portions of the patient's anatomy of interest. For example, the cross-sectional images can be processed by segmentation, which generally involves separating objects not of interest from objects of interest, e.g., extracting anatomical surfaces, structures, or regions of interest from the images for the purposes of anatomical identification, diagnosis, evaluation, and volumetric measurements. In detecting tumor changes with therapies, volumetric measurement can be more accurate and sensitive than conventional linear measurements. 3D segmentation of cross-sectional images provides a feasible way to quantify tumor volume and volume changes over time.

Most abdominal CT-scans are acquired after contrast enhancement at the "portal venous phase" (PVP). The PVP acquisition usually uses a fixed delay time after contrast injection. This parameter is set based upon the CT scanner characteristics and is not tailored for a patient's body habitus or cardiovascular system. This leads to a variability in timing and enhancement Optimal PVP timing is crucial in oncology for the automatic detection and characterization of lesions, as well as the estimation of tumor enhancement or vascularity, which is increasingly being used to predict treatment response, as well as outcome and recurrence.

SUMMARY

Techniques are provided for measuring vascular density in a subject.

In a first set of embodiments, a method for measuring post contrast phase, includes collecting three dimensional (3D) medical imagery of a subject using a 3D medical imaging device after injecting the subject with a contrast agent. The method also includes selecting a first set of one or more slices displaced in the axial direction, wherein each slice in the set includes a first anatomical feature selected from a group consisting of an aorta, a portal vein, an inferior vena cava, a liver, a spleen and a renal cortex. The method further includes; selecting a second set of one or more slices displaced in the axial direction, wherein each slice in the second set includes a different second anatomical feature selected from the group. Still further, the method includes selecting a first image region on a first slice of the first set and a different second image region on a second slice of the second set. The first image region includes the first anatomical feature and the second image region includes the different second anatomical feature. Even further, the method includes using a first trained convolutional neural network on a processor with input based on the first image region and the second image region to determine automatically on the processor a post contrast phase. The first trained neural network includes: a first plurality of convolutional hidden layers operating on the first image region; a second plurality of convolutional hidden layers operating on the second image region; and at least one fully connected hidden layer receiving output from each of the first plurality of convolutional hidden layers and the second plurality of convolutional hidden layers and outputting to an output layer one or more nodes each representing a probability of a post contrast phase. Yet further still, the method includes presenting automatically, on a display device, output data based on the post contrast phase.

In various other embodiments of the first set, said selecting the first image region is performed automatically on the processor using a second trained convolutional neural network with first input based on a set of one or more contiguous slices of the 3D medial imagery; and, said selecting the second image region is performed automatically on the processor using a different third trained convolutional neural network with second input based on the set of one or more contiguous slices of the 3D medial imagery. In some of these embodiments, the method includes determining the first set of one or more contiguous slices automatically on the processor using a different fourth trained convolutional neural network with first input based on the 3D medial imagery and output that indicates a probability that each slice includes the first anatomical feature.

In various other embodiments of the first set, the output data comprises an image of vascular density; or the output data comprises a set of output images displaced in the axial direction of vascular density; or the output data comprises a set of output images displaced in the axial direction of a tumor density or a tumor boundary; or the output data indicates a tumor density or a tumor boundary.

In other sets of embodiments, a computer-readable medium, or a neural network apparatus, or a system is configured to perform one or more steps of one or more of the above methods.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which.

DETAILED DESCRIPTION

A method and apparatus are described for objectively measuring vascular density in an organ. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" for a positive only parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described in detail below in the context of CT scans and using portal vein and aorta regions of certain axial slices. However, the invention is not limited to this context. In other embodiments the same techniques are applied to a set of axially displaced slices from any three dimensional (3D) medical imaging device when using a contrast agent, including Magnetic Resonance Imaging (MRI) devices and other anatomical regions selected two or more at a time among the aorta, portal vein, inferior vena cava, liver, spleen and renal cortex.

1. OVERVIEW

Figure 1A:
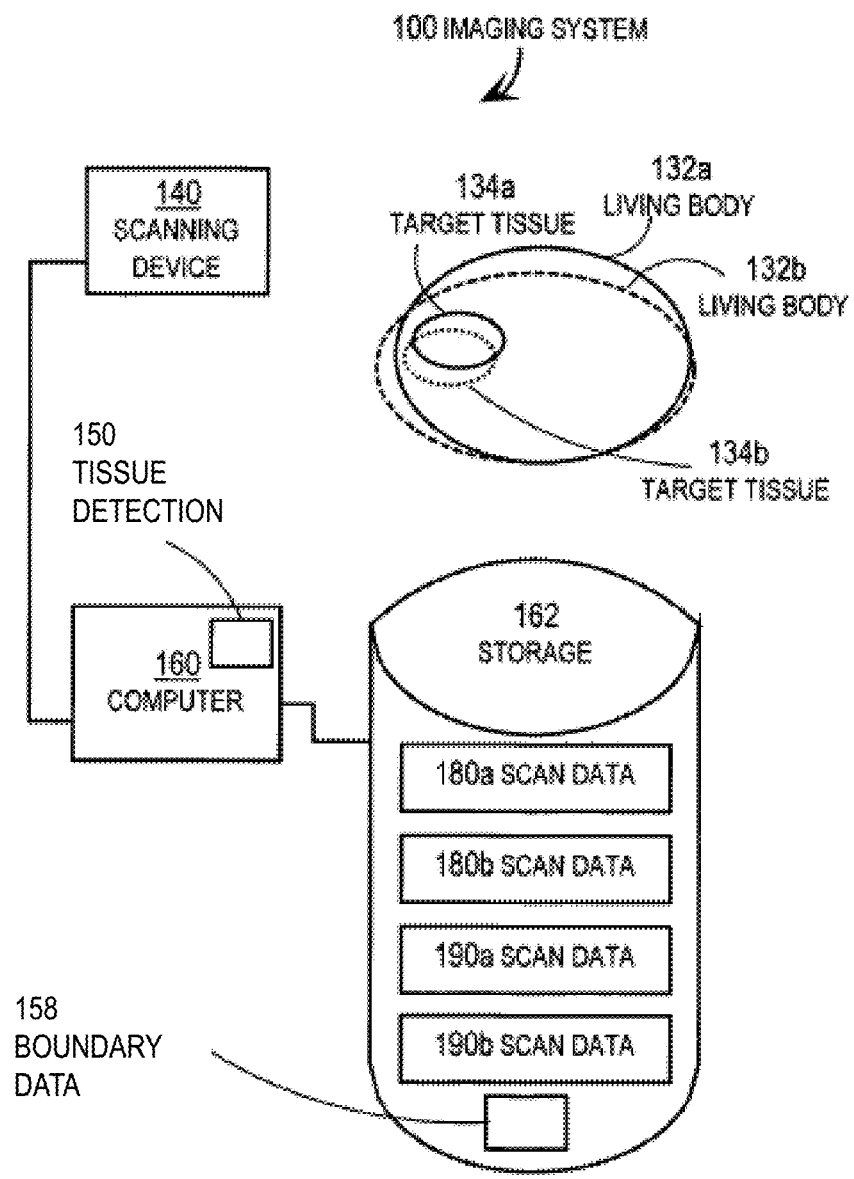
FIG. 1A is a block diagram that illustrates an imaging system for tissue detection, according to an embodiment.

FIG. 1A is a block diagram that illustrates an imaging system 100 for tissue detection, according to an embodiment. The system 100 is designed for determining the spatial arrangement of soft target tissue in a living body. For purposes of illustration, a living body is depicted, but is not part of the system 100. In the illustrated embodiment, a living body is depicted in a first spatial arrangement 132a at one time and includes a target tissue in a corresponding spatial arrangement 134a. At a different time, the same living body is in a second spatial arrangement 132b that includes the same or changed target tissue in a different corresponding spatial arrangement 134b.

In the illustrated embodiment, system 100 includes a scanning device 140, such as a full dose X-ray computed tomography (CT) scanner, or a magnetic resonance imaging (MRI) scanner, among others. In some embodiments, the scanning device 140 is used at one or more different times. The device 140 is configured to produce scanned images that each represent a cross section of the living body at one of multiple cross sectional (transverse) slices arranged along the axial direction of the body, which is oriented in the long dimension of the body.

In system 100, data from the imager 140 is received at a computer 160 and stored on storage device 162. Computer systems and storage devices like 160, 162, respectively, are described in more detail below with reference to FIG. 5 and FIG. 6. Scan data 180a, 180b, 190a, 190b based on data measured at imager 140 at one or more different times or axial locations or both are stored on storage device 162. For example, scan data 180a and scan data 180b, which include scanned images at two slices separated in the axial direction, is stored based on measurements from scanning device 140 at one time. Scan data 190a, 190b, which include scanned images at two slices separated in the axial direction, is stored based on measurements from scanning device 140 at a different time.

In various embodiments, a tissue detection process 150 operates on computer 160 to determine a boundary between scan elements of scan data which are inside and outside a particular target tissue or cell. The boundary data is stored in boundary data 158 in associations with the scan data, e.g., scan data 180a, 180b, 190a, 190b.

Although processes, equipment, and data structures are depicted in FIG. 1A as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts. For example, although system 100 is depicted with a particular number of scanning devices 140, computers 160, and scan data 180, 190 on storage device 162 for purposes of illustration, in other embodiments more or fewer scanning devices, computers, storage devices and scan data constitute an imaging system for determining spatial arrangement of tissues, including cells.

Figure 1B:
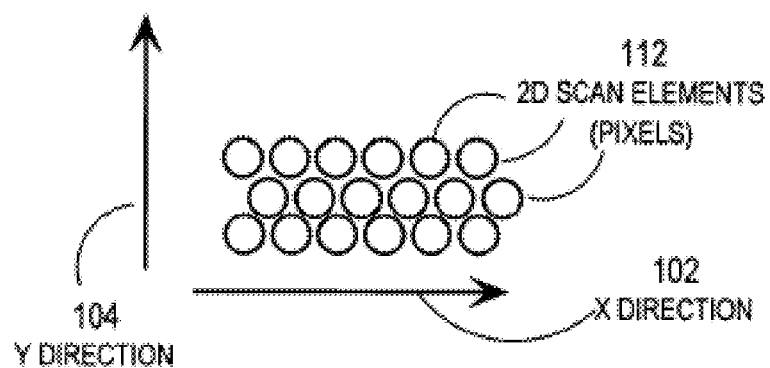
FIG. 1B is a block diagram that illustrates scan elements in a 2D scan, such as one scanned image from a CT scanner.

FIG. 1B is a block diagram that illustrates scan elements in a 2D scan 110, such as one scanned image from a CT scanner. The two dimensions of the scan 110 are represented by the x direction arrow 102 and the y direction arrow 104. The scan 110 consists of a two-dimensional array of 2D scan elements (also called picture elements and abbreviated as pixels) 112 each with an associated position. Typically, a 2D scan element position is given by a row number in the x direction and a column number in the y direction of a rectangular array of scan elements. A value at each scan element position represents a measured or computed intensity or amplitude that represents a physical property (e.g., X-ray absorption, or resonance frequency of an MRI scanner) at a corresponding position in at least a portion of the spatial arrangement 132a, 132b of the living body. The measured property is called amplitude hereinafter and is treated as a scalar quantity. In some embodiments, two or more properties are measured together at a pixel location and multiple amplitudes are obtained that can be collected into a vector quantity, such as spectral amplitudes in MRSI. Although a particular number and arrangement of equal sized circular scan elements 112 are shown for purposes of illustration, in other embodiments, more elements in the same or different arrangement with the same or different sizes and shapes are included in a 2D scan.

Figure 1C:
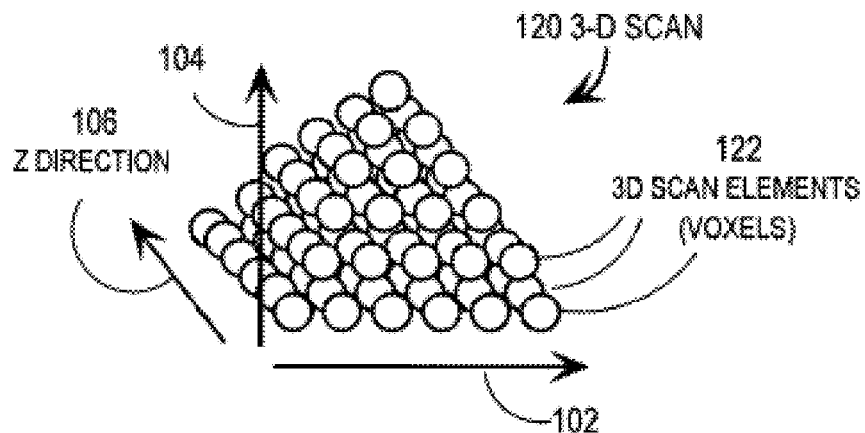
FIG. 1C is a block diagram that illustrates scan elements in a 3D scan, such as stacked multiple scanned images from a CT imager or true 3D scan elements from volumetric CT imagers or ultrasound.

FIG. 1C is a block diagram that illustrates scan elements in a 3D scan 120, such as stacked multiple scanned images from a CT imager or true 3D scan elements from volumetric CT imagers or MRI or US. The three dimensions of the scan are represented by the x direction arrow 102, the y direction arrow 104, and the z direction arrow 106. The scan 120 consists of a three-dimensional array of 3D scan elements (also called volume elements and abbreviated as voxels) 122 each with an associated position. Typically, a 3D scan element position is given by a row number in the x direction, column number in the y direction and a scanned image number (also called a scan number) in the z (axial) direction of a cubic array of scan elements or a temporal sequence of scanned slices. A value at each scan element position represents a measured or computed intensity that represents a physical property (e.g., X-ray absorption for a CT scanner, or resonance frequency of an MRI scanner) at a corresponding position in at least a portion of the spatial arrangement 132a, 132b of the living body. Although a particular number and arrangement of equal sized spherical scan elements 122 are shown for purposes of illustration, in other embodiments, more elements in the same or different arrangement with the same or different sizes and shapes are included in a 3D scan.

The term voxels is used herein to represent either 2D scan elements (pixels) or 3D scan elements (voxels), or 4D scan elements, or some combination, depending on the context.

Amplitude is often expressed as one of a series of discrete gray-levels. A grey-level image may be seen as a topographic relief, where the grey level of a voxel is interpreted as its altitude in the relief. A drop of water falling on a topographic relief flows along a path to finally reach a local minimum. Intuitively, the watershed of a relief corresponds to the limits of the adjacent catchment basins of the drops of water. For segmentation purposes, it is common to interpret the horizontal gradient of the grayscale image as elevation information. The horizontal gradient is expressed as a two-element vector at each voxel, the magnitude and direction of the steepest increase in amplitude from the voxel to any of its neighbors. In various arrangements, called lattices, a voxel may have one, two, four, six, eight or more neighbors. Intuitively, a drop of water falling on a topographic relief flows towards the "nearest" minimum. The "nearest" minimum is that minimum which lies at the end of the path of steepest descent. In terms of topography, this occurs if the point lies in the catchment basin of that minimum. The length of that path weighted by the altitude drop is related to the topographical distance, as described in more detail below.

Figure 2A:
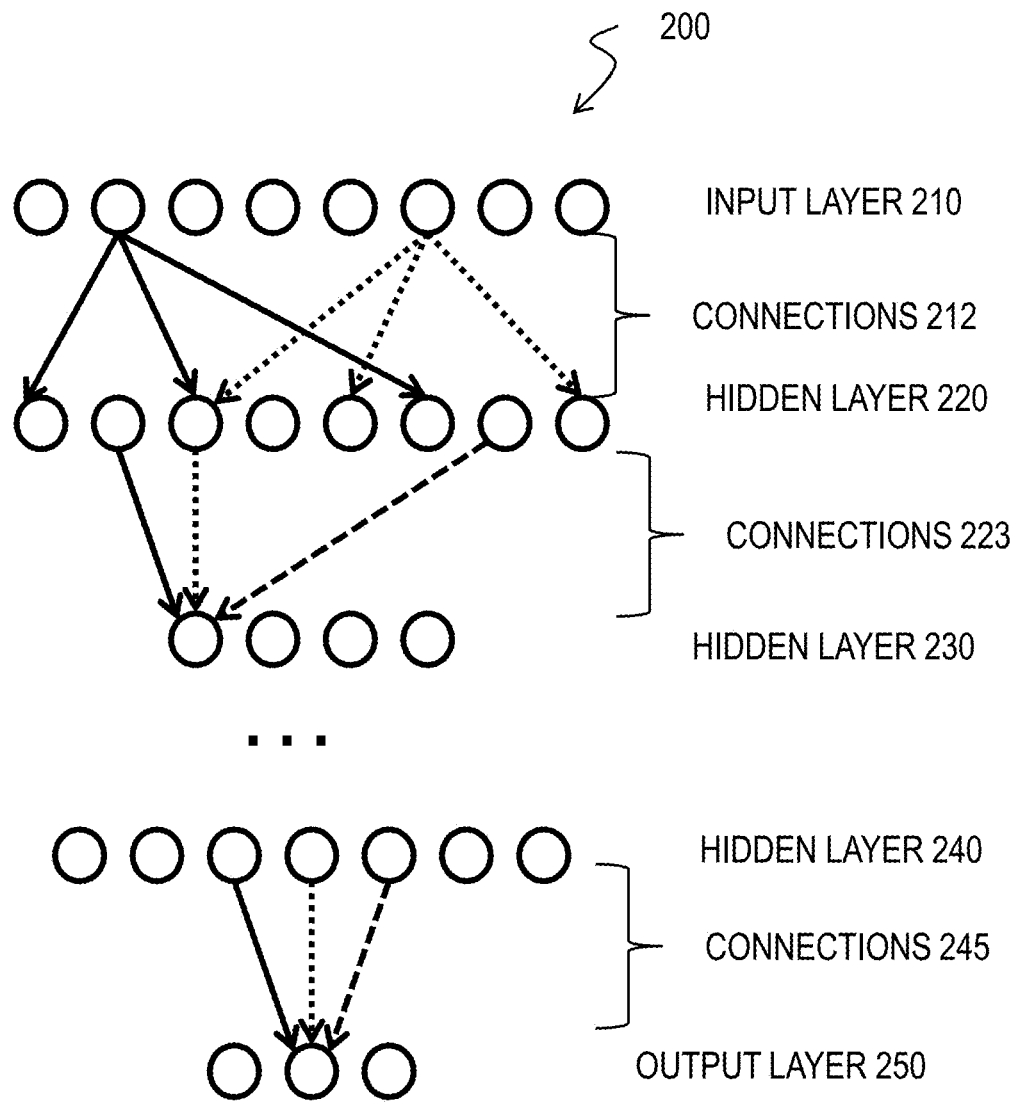
FIG. 2A is a block diagram that illustrates example flow structure of a generic neural network computation.

FIG. 2A is a block diagram that illustrates example flow structure of a generic neural network computation. A neural network is a computational system, implemented on a general=purpose computer or application specific integrated circuit (ASIC) or field programmable gate array (FPGA) or other hardware, which is made up of an input layer of nodes, at least one hidden layer of nodes, and an output layer of one or more nodes. Each node is an element, such as a register or memory location, that holds data that indicates a value. The value can be code, binary, integer, floating point or any other means of representing data and can be a scalar or vector or tensor. Values in nodes in each successive layer after the input layer in the direction toward the output layer is based on the values of one or more nodes in the layer before. The nodes in one layer that contribute to the next layer are said to be connected to the node in the later layer. The values of the connected nodes are combined at the node in the later layer using some activation function with scale and bias (also called weights) that can be different for each connection. Neural networks are so named because they are modeled after the way neuron cells are connected in biological systems. A fully connected neural network has every node at each layer connected to every node at any previous or later layer.

For example, the neural network 200 depicted in FIG. 2A has an input layer 210 of eight nodes, each node represented by an open circle. The network 200 includes hidden layers 220, 230 and 240, among zero or more others indicated by ellipsis, and an output layer 250 of three nodes. The output layer nodes hold values that represent the result of the neural network computation for three parameters. FIG. 2A also shows a few example connections as arrows connecting a node in one layer with one or more nodes in a later layer. All connections inherent in a fully connected version of the depicted network are not shown in order to avoid obfuscating the illustration. On node in input layer 210 is connected to three nodes in hidden layer 220 by three connections represented by solid arrows; and, another node in input layer 210 is connected to three nodes in hidden layer 220 by three connections represented by three dotted arrows. In other embodiments each node in one layer is connected to more or fewer nodes in the next layer. Each node in a later layer thus has a value based on all the nodes that are connected to it, as illustrated for one node in hidden layer 230, which has a value based on a combination of values in three nodes in the previous layer, represented by a solid arrow, dotted arrow and dashed arrow. In other embodiments each node in one layer combines values from more or fewer nodes in the previous layer.

Figure 2B:
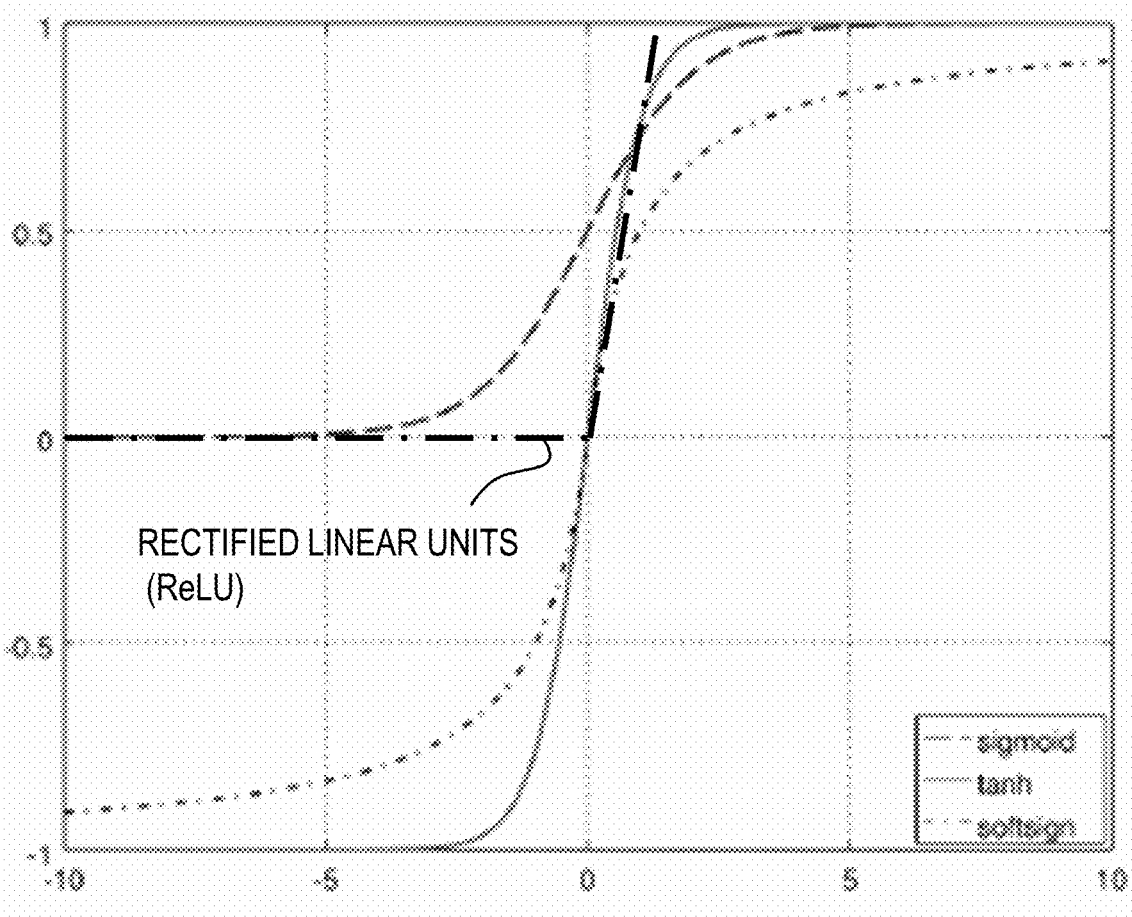
FIG. 2B is a plot that illustrates example activation functions used to combine inputs at any node of a neural network.

FIG. 2B is a plot that illustrates example activation functions used to combine inputs at any node of a neural network. These activation functions are normalized to have a magnitude of 1 and a bias of zero; but when associated with any connection can have a variable magnitude given by a weight and centered on a different value given by a bias. The values in the output layer 250 depend on the activation functions used at each node and the weights and biases associated with each connection that terminates on that node. The sigmoid activation function (dashed trace) has the properties that values much less than the center value do not contribute to the combination (a so called switch off effect) and large values do not contribute more than the maximum value to the combination (a so called saturation effect), both properties frequently observed in natural neurons. The tan h activation function has similar properties but allows both positive and negative contributions. The softsign activation function is similar to the tan h function but has much more gradual switch and saturation responses. The rectified linear units (ReLU) activation function simply ignores negative contributions from nodes on the previous layer, but increases linearly with positive contributions from the nodes on the previous layer; thus, ReLU activation exhibits switching but does not exhibit saturation. In some embodiments, the activation function operates on individual connections before a subsequent operation, such as summation or multiplication; in other embodiments, the activation function operates on the sum or product of the values in the connected nodes. In other embodiments, other activation functions are used, such as kernel convolution.

An advantage of neural networks is that they can be trained to produce a desired output from a given input without knowledge of how the desired output is computed. There are various algorithms known in the art to train the neural network on example inputs with known outputs. Typically, the activation function for each node or layer of nodes is predetermined, and the training determines the weights and biases for each connection. A trained network that provides useful results, e.g., with demonstrated good performance for known results, is then used in operation on new input data not used to train or validate the network.

In image processing, it was found that neural networks configured to perform convolution over relatively small two-dimensional portions of an image, called the receptive field, provided superior results with smaller networks. Here each input layer node corresponds to one or more pixels or voxels in an input image. Such neural networks are called convolution neural networks (CNN) and are modeled after the neurons in the visual cortex of animals. As in the biological models, receptive fields of different neurons partially overlap such that they cover the entire visual field. In such neural networks, not only the activation function, but also the weights and biases, are shared for an entire layer. This provides the networks with shift and rotation invariant responses. The hidden layers of a CNN typically consist of convolutional layers, pooling layers, fully connected layers and normalization layers. The convolutional layer has parameters made up of a set of learnable filters (or kernels), which have a small receptive field (e.g., 3×3). The filter is used for one or more of blurring, sharpening, embossing, edge detection, among others. This is accomplished by doing a convolution between the filter and the receptive field. In a convolution layer, each filter is convolved across the width and height of the previous layer, e.g., the input image, computing the dot product between the entries of the filter and the previous layer nodes and producing a 2-dimensional activation map of that filter. The same kernel, weights and biases are used for every node in the layer. In a pooling layer, the activation functions perform a form of non-linear down-sampling, e.g., producing one node with a single value to represent four nodes in a previous layer. There are several non-linear functions to implement pooling among which max pooling is the most common. A normalization layer simply rescales the values in a layer to lie between a predetermined minimum value and maximum value, e.g., 0 and 1, respectively.

Figure 3A:
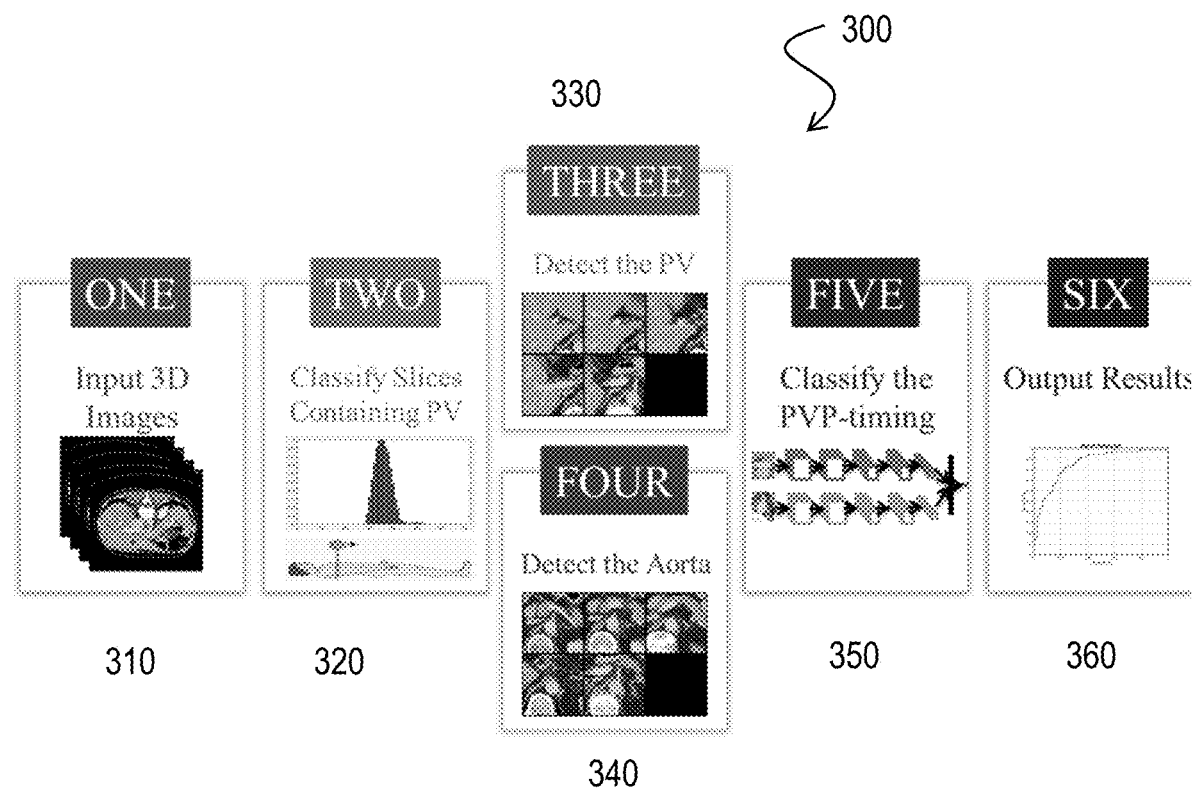
FIG. 3A is flow diagram that illustrates an example method for objectively and automatically determining and using probability of optimal timing of 3D images after contrast, according to an embodiment.

FIG. 3A is flow diagram that illustrates an example method for objectively and automatically determining and using post contrast phase information, such as probability of optimal timing of 3D images after contrast, according to an embodiment. Although steps are depicted in FIG. 3A as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

Figure 3B:
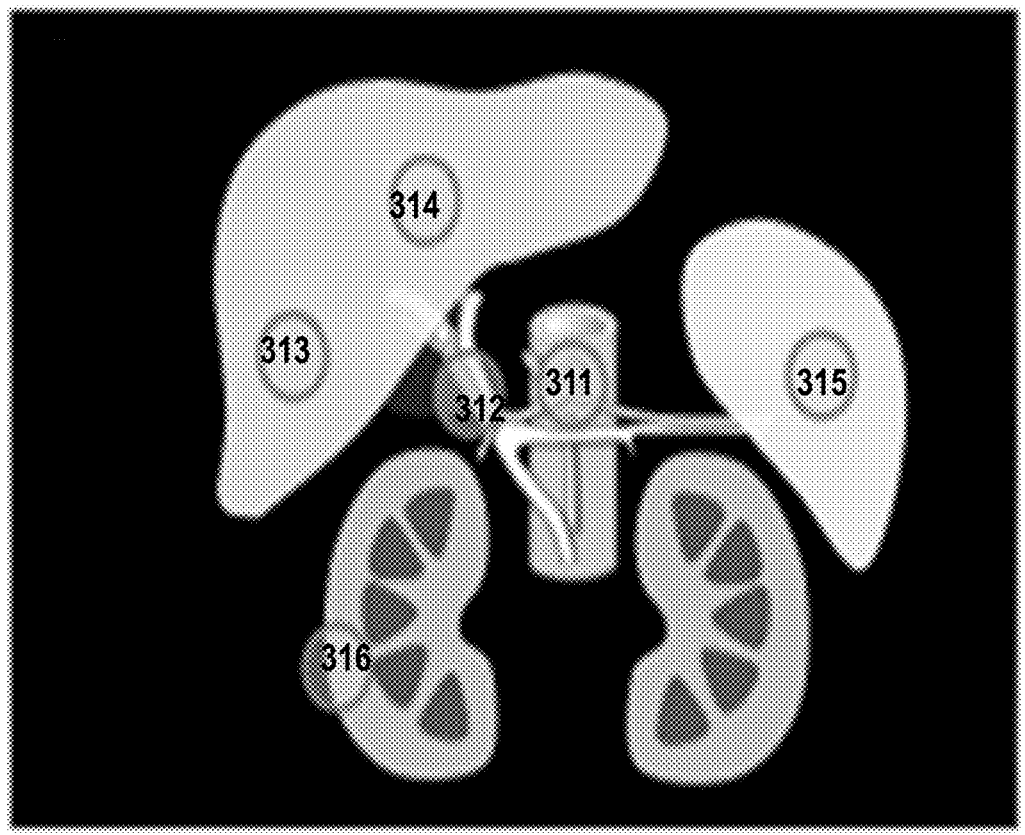
FIG. 3B is a block diagram that illustrates anatomical features often found in 3D imagery and used in automatic detection of phase, according to various embodiments.

Step ONE (3101). Three dimensional (3D) medical imagery of a subject is collected using a 3D medical imaging device after the subject is injected with a contrast agent. For example, volumetric data from a contrast enhanced abdominal CT scan is collected, as described in the examples section. The post contrast phase has been found to be evident in manual comparisons among six anatomical features, depicted in FIG. 3B. FIG. 3B is a block diagram that illustrates anatomical features often found in 3D imagery and used in automatic detection of phase, according to various embodiments. The anatomical features used in various embodiments include the aorta 311, the portal vein 312, the inferior vena cava 313, the liver 314, the spleen 315, and the renal cortex 316.

Step TWO (320). A first trained convolutional neural network is used on a processor with first input based on the 3D medial imagery to select a set of one or more contiguous slices displaced in the axial direction, in which each slice in the set includes a first anatomical feature selected from a group consisting of an aorta, a portal vein, an inferior vena cava, a liver, a spleen and a renal cortex. In an example embodiment, the publically available Alex-net CNN is trained to recognize slices that include a portal vein and serve as the first CNN, with portal vein serving as the first anatomical feature. Alex-net performs binary classification using a single node output layer with a value that indicates probability of being in the target class. A training set of over a hundred images is assembled in which the presence or absence of the portal vein has been determined by an expert radiologist. Alex-net is composed of 5 convolutional layers followed by 3 fully connected layers. The default input for Alex-net is an image of size 227×227 and 3 channels. Hence, in an illustrated embodiment, each 3D image slice was preprocessed to the default input of Alex-net. The preprocessing included the following steps. 1) Interpolate each 3D image into spacing matching the minimum spacing in the training set. 2) Normalize the 3D image to an amplitude range of 0 to 255. 3) Centrally crop the image to size 554×554 pixels including as much of the internal structure of the subject as possible. 4) Down-sample each axial slice of the 3D image by a factor of 2 to size 227×227 pixels which is the input size of Alex-net (and the faster R-CNN that is also publicly available). 5) Insert one slice into the second channel of the 3 Alex-net channels, and two other nearby slices (e.g., slices 5 mm above and below the slice in channel 2) to the first and third channel of the Alex-net input layer, respectively.

Training Alex-net to be the first CNN was performed by using the training images after the preprocessing. Slices with the annotated portal vein label were used as positive samples, while images at least 25 mm away from annotated images are used as negative samples for training. Negative samples equal to the number of positive samples are randomly selected. A data augmentation technique for training can be applied to increase training samples five times by allowing random rotations up to 10 degrees and random shifts up to 10-pixel shifts. Alex-net was trained using the stochastic gradient descent with the momentum of 0.9, 512 mini batch size, 10 epochs, and $10^{-6}$ learning rate. In experimental embodiments, 2690 positive samples and 2690 negative samples were found useful to fine-tune Alex-net.

In other embodiments another publicly available or private CNN is used; and, preprocessing and training is changed to accommodate the parameters for that CNN, for the same or for a different anatomical feature, as is readily understood by a person of ordinary skill in the art.

After training, the first CNN net is used to operate on each slice of a clinical 3D image after the preprocessing described above.

Step THREE (330). A different second trained convolutional neural network on the processor is used with second input based on the set of contiguous slices to select a first image region on the set of one or more contiguous slices. The first image region includes the first anatomical feature. In an example embodiment, detection of an anatomical feature's image region is performed during Step THREE (330) with the second CNN. For example, publically available Faster R-CNN is used, which is a deep-learning based object detection system with high performance to run at near real-time frame rates to detect an object, such as one of the anatomical features, in an image. The output layer of the Faster R-CNN is a bounding box that contains the most likely occurrence of a learned object in the image, if any. A bounding box is a data structure that includes coordinates for a pixel of one corner of a box, a box size, and a probability of the object being in the box. This bounding box output of Faster R-CNN is used as the image region for a particular anatomical feature.

For example, the training samples for the Faster R-CNN in this step are 3D image slices containing portal vein and portal vein's contour. The training set can be augmented from the slices annotated with portal vein contours using random shifts and rotations. In the experimental embodiments, the Faster R-CNN applied pre-trained publicly-available Cifar-Net as the backbone and was trained by using the stochastic gradient descent with momentum optimizer with parameters of 0.9 momentum, 256 mini batch size, 10 epochs, and $10^{-5}$ learning rate. The five bounding-boxes with highest probability values for the portal vein are included in the images used in the Step SIX (360), described below.

In experimental embodiments, over 500 slices with portal veins and contours were sufficient with augmentation to train the second neural network for portal vein boundary box.

If there are fewer than five bounding boxes with a probability over a threshold, all of the bounding boxes with probability over the threshold are used in Step SIX (360) described below. In an example embodiment, the threshold probability for finding the portal vein is 0.85. The five slices with the best probability, including the first anatomical feature, need not be consecutive or contiguous.

In other embodiments another publically available or private CNN is used and preprocessing and training is changed to accommodate the parameters for that CNN, as is readily understood by a person of ordinary skill in the art.

Step FOUR (340). Detection of a second image region by its bounding-boxes parallels the detection of the first bounding box described in Step THREE (330). The publicly available Faster R-CNN is used. The second image region on the set of one or more contiguous slices includes a different second anatomical feature selected from the group consisting of the aorta, the portal vein, the inferior vena cava, the liver, the spleen and the renal cortex.

In an example embodiment, the training samples for Faster R-CNN in this step are 3D image slices containing the aorta and the aorta's contour. The training set can be augmented from the slices annotated with aorta contours using random shifts and rotations. In the experimental embodiments, the Faster R-CNN applied pre-trained publicly-available Cifar-Net as the backbone and was trained by using the stochastic gradient descent with momentum optimizer with parameters of 0.9 momentum, 256 mini batch size, 10 epochs, and $10^{-5}$ learning rate. The five bounding-boxes with highest probability values for the aorta are included in the images used in the next step, step five.

Figure 4:
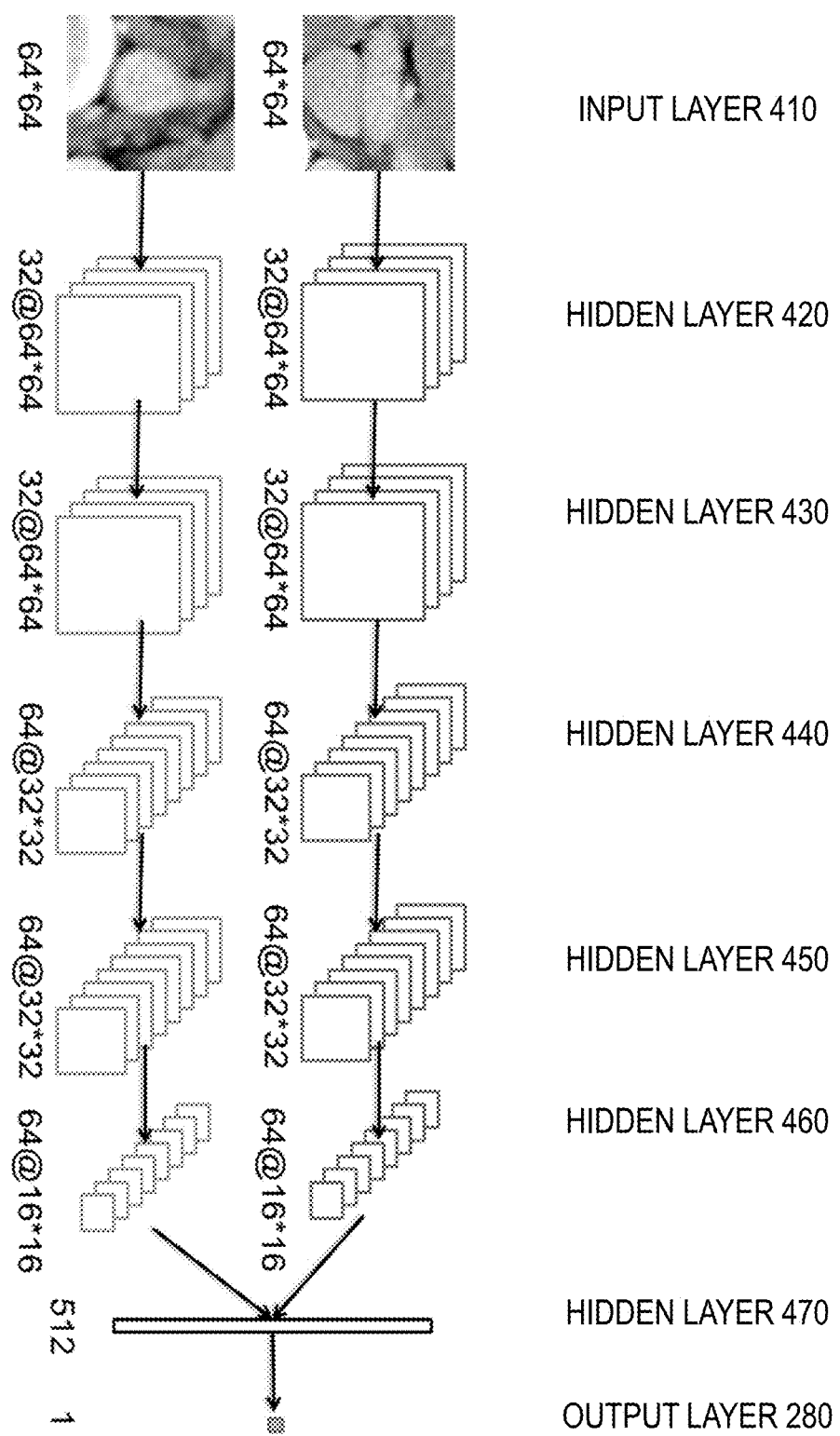
FIG. 4 is block diagrams that illustrate example neural networks that determines post contrast phase based on an image of portal vein and an image of an aorta for a subject, according to an embodiment.

Step FIVE (350). A different third trained convolutional neural network on the processor is used with third input based on the first image region and the second image region to determine a post contrast phase. Inherently, this post contrast phase is based on features in the image values in the first image region and the second image region. In an experimental embodiment, a new dual CNN was designed and trained as shown in FIG. 4, to process image patches (using the image slice and the bounding box masks) of portal vein and aorta. So the input layer includes nodes representing the pixels in the portal vein bounding box and the aorta bounding box. In some embodiments, the input layer includes 64×64×2 nodes. Then the image patch for the portal vein is centered in the first 64×64 nodes and any node without a corresponding pixel in the image patch is padded with zeros or any pixels in the bounding box outside the center 64×64 are omitted. Similarly, the image patch for the aorta is centered in the second 64×64 nodes. The output of this CNN is a one or more nodes that holds corresponding values that indicate probability of corresponding one or more post contrast phases. In one embodiment, the output layer comprises a single node that indicates the probability of optimal timing.

FIG. 4 is block diagram that illustrates an example neural network that determines probability of one or more post contrast phases based on an image of portal vein and an image of an aorta for a subject, according to an embodiment. This is an example of a neural network used in step five (350). In this network, two blocks of two consecutive convolutional layers with 32 and 64 filters, respectively, were used. Each filter had 3×3×N pixels convolutional kernels with ReLU activation, and zero padding on the edge, where N is the number of filters in previous layer and N=1 for the first hidden layer. Thus, hidden layer 420 has two different sets of 32×64×64 nodes. The first set of 32×64×64 nodes in hidden layer 420 are based on the 64×64 nodes of the first image region (e.g., portal vein) each convolved with a different one of the 32 filters. The second set of 32×64×64 nodes in hidden layer 420 are based on the 64×64 nodes of the second image region (e.g., aorta) each convolved with a different one of the 32 filters. The next hidden layer 430 also has two sets of 32×64×64 nodes resulting from a second consecutive application of the same 32 filters. That is, the output of the first filter is again convolved with the first filter but using a filter size of 3×3×32, and the output of the second filter is again convolved with the second filter, and so on for all 32 filters and for both image regions (portal vein and aorta patches).

The next hidden layer 440 applies 64 filters to the 32 sets of 64×64 nodes in layer 430 for each of the two image regions after downsizing the 64×64 nodes of the previous layer by a factor of 2, using max pooling, to 32×32 nodes. Thus, the filter kernel is 3×3×32 and outputs a layer of 64×32×32 nodes. The next hidden layer 450 has two sets of 64×32×32 nodes resulting from a second consecutive application of the same 64 filters and a kernel of 3×3×64. That is, the output of the first filter is again convolved with the first filter, and the output of the second filter is again convolved with the second filter, and so on for all 64 filters and for both image regions (portal vein and aorta patches).

Each block was followed by a 2×2 (factor of 2) max-pooling layer and a dropout layer of dropout rate 50% to produce hidden layer 460. Finally, the fully connected hidden layer 470 has 512 nodes combining the information about the two image regions (e.g., portal vein and the aorta). The final output layer 280 is fully connected with the previous layer with sigmoid activation and produces a probability for each of one or more post contrast phases. In the depicted embodiment, the output layer 280 has a single node (only one node) that contains a value indicating the probability of optimal post contrast phase.

In an experimental embodiment, this network is trained using stochastic gradient descent optimizer with the momentum of 0.9, 128 mini batch size, 100 epochs, and 0.01 learning rate. Over 400 training images were successfully used to train this network.

In other embodiments other numbers of hidden layer and other numbers and types of filters are used in each layer and blocks are arranged in a different fashion. The design of the presented and any alternative CNN is governed by the objective to locate the important features separately within each image region and derive the mean density associated with the feature separately as well; and, only after that do a comparison between the two separate image regions. Locating the features (such as the portal vein or aorta blood vessels) involves many layers at successively deep layers. Training very deep layers typically involves millions of training samples; but, medical images are hard to collected and label. Typically, only hundreds of training samples are available. This forces the number of layers to be as small as possible. The experimental embodiments have shown that four convolution layers (or two to eight layers in other embodiments) provide a good compromise between feature detection (large depth) and available images for training (small depths).

Calculating the mean density can be advantageously performed with only one or two layers. So, the feature detection and density determination are done in parallel for the two image regions separately, e.g., without nodes in any layer connected to upper nodes from different image regions. The number and type of filters applied in each of these layers are typical of what has been effective in CNN of image data. The two different image regions are processed separately to derive the feature and corresponding density. After these layers, the next layers have nodes that combine information from both image regions. Thus, the final one or more layers are used to detect the density difference between the two different image regions by using connections from both image regions to each node. It is advantageous for these last one or few layers to be fully connected and let the training discover the important connections.

In some embodiments, there is a separate node in the last layer to express the probability of each phase to be detected, such as these five phases: no contrast 'NC'; early aorta phase 'Early AP'; optimal aorta phase 'Optimal AP', optimal portal vein phase 'Optimal PVP'; and late portal vein phase 'Late PVP' described in some embodiments.

Step SIX (306). The post contrast phase is used to produce output data that is presented or used to operate some equipment. In some embodiments, the optimal PVP probability is the average of several scores resulted from several pairs of image regions (e.g., five portal vein bounding boxes and five aorta bounding-boxes). For example, in some embodiments, the up to five scores obtained by using the up to five portal vein image patches and corresponding aorta image patches are averaged together. This is advantageous as it reduces noise and uncertainty in the determination of optimal timing probability. In some embodiments, the output layer 280 includes more nodes, each describing the raw score for a different timing phase post contrast, such as; early, optimal and late; or, too early, early but correctable by factor X, optimal, late but correctable by factor Y, and too late, where factor X and factor Y are parameters of the classification determined by experiment, e.g., by taking 3D medical imagery at multiple times post contrast and comparing vascular density from the optimal scan to vascular density from earlier and later scans. In The examples section, details are given for determining five phases, termed: no contrast 'NC'; early aorta phase 'Early AP'; optimal aorta phase 'Optimal AP', optimal portal vein phase 'Optimal PVP'; and late portal vein phase 'Late PVP'.

In various other embodiments, the output data produced in step six 360 comprises an image of vascular density in the organ; or the output data comprises a set of output images displaced in the axial direction of vascular density; or the output data comprises a set of output images displaced in the axial direction of a tumor boundary based on vascular density in the organ; or the output data indicates a volume of a tumor based a tumor boundary that is based on vascular density in the organ in a set of images displaced in the axial direction.

In some embodiments, by knowing the probability of one or more post contrast phases, a correction factor can be applied to the vascularity or size of the dense volume so that tumor properties derived from 3D images take at non-optimal times can be compared to tumor properties from images that are taken at optimal times. In some embodiments, the probability is used simply to determine if another scan should be taken of the current subject at a later time.

2. EXAMPLE EMBODIMENTS

Example embodiment using CT scans for detecting liver metastasis are described in more detail in this section. In some example embodiments, the output is just a probability of optimal timing. In other embodiments, the probability of each of two or more phases, or the most probable non-optimal phase, is determined In one embodiment, the probabilities of five post contrast phases are produced in the output layer 280.

2.1 Example A

In this example, 700 CTs acquired at the portal venous phase had their contrast timing determined by a consensus reading between experienced radiologists. Patients were divided between optimal-timing (n=443) vs non-optimal timing (early or late, n=257). These timing data were used as the reference standard for the automated timing classification system. The whole 3D voxel images (normalized to 512*512*150) were used directly as input to a deep learning method (CNNs) to maximally explore the potential imaging features. The proposed network consisted of 5 convolutional layers and Leaky ReLU activations, followed by average pooling layers and three dense layers. The outputs were equivalent to the classes: optimal and non-optimal. To train and evaluate the CNN we used a dataset of 700 CTs, within which 600 (396:204) were used as training and validation. The remaining 100 (57:43) were not included in the training set and were thus totally blind to the computer when used for testing. Five-fold cross validation was used to assess performance.

The classification performances were 89.3% (SE:0.01) in the training set and 93.2% (SE:0.01) in the validation set, which demonstrated the potential of CNNs in automatically analyzing contrast enhancement timing classification in CT scans.

It is concluded that there is great potential for the application of deep learning methods as an aid to radiologists in the analysis of medical images. Larger datasets with a wider spectrum of timing will be needed to refine performance and the learned imaging features needed to be examined.

The clinical relevance/application is that an immediate, unbiased appraisal of contrast timing can reduce medical error because certain pathologies are invisible outside of the appropriate contrast phase.

2.2 Example B

In this example, we designed a fully automatic quality control algorithm. A 6 steps strategy was used based on our previous work which indicated that the two key factors for the identification of an optimal PVP-timing are the density in the aorta and in the portal vein.

We uploaded CT-scan images. The software located the PV slices. Then the Portal Vein was detected by the software, as well as the aorta. Finally the software classified the PVP-timing and the output was a probability that the PVP timing is optimal. Training set was made up of 479 CT-scans. Testing set was made up of 203 CT-scans Our pipeline outputs a probability (0-100%) of optimal PVP timing.

The first step is to input the whole CT scans. We used DICOM images. The complete series was analyzed by our algorithm using a soft tissue window going from −50 HU to +350 HU The second step was to locate the slice containing the portal venous slice. We used pre-trained CNN features from Alexnet. Pre-trained CNN features allowed for the successful location of the slices containing portal vein with an accuracy of 85%. This is the limiting step in this embodiment; but, can be improved for other embodiments. The third step was to locate the portal vein. The algorithm locates the portal veins and computes probabilities. In this patient, the algorithm found 5 slices including the portal vein. The probability was above 0.88. in these slices with Faster RCNN. 12 The fourth step was to locate the aorta. The algorithm located the aorta and computed probabilities. In this patient, the algorithm found many slices including the aorta. The probability was 100%.

We explained previously that the algorithm was able to detect the portal vein and the aorta. The algorithm automatically placed two patches of 64*64 pixels in the portal vein and in the aorta, one each. We then trained a CNN to classify the PVP timing according to these two patches. We used a dual input neural network to estimate if each patient had an optimal PVP-timing or a non-optimal PVP-timing. This network contains 4 convolution layers (kernel is 3*3). The fully connected layer combines the information of portal vein and aorta. First, the software analysed a 64*64 voxels patch in the aorta and in the portal vein. Then, two consecutive convolutional layers with 32 filters were used. Each filter had 3×3 pixels convolutional kernels with ReLU activation (truncate all negative value to zero), zero padding on the edge, followed by max-pooling and dropout (prevent overfitting). Then, two consecutive convolutional layers with 64 filters were used using similar strategies. Finally, the fully connected layer included 512 nodes and combined the information aboPerformance measures were the ut the portal vein and the aorta. The final 1 node layer was connected with the previous layers (with sigmoid activation). Stochastic gradient descent optimizer (SGD) were applied to train the model. The Loss function used binary-cross-entropy.

We trained the model with 128 mini batch size and 100 epochs network. The testing sets included 203 patients The overall accuracy of this fully automatic quality control algorithm (Deep-learning) was determined using receiver operating characteristic (ROC, true positive rate versus false positive rate for binary classifier) and area under ROC (AUR). The AUC was 0.84. For an unrelated variable, AUC=0.5. For a perfect classifier AUC=1.0. As a comparison, our benchmarks are: Visual assessment by trained radiologist has an AUC=0.82; semi-automatic regions of interest (ROIs) has an AUC=0.89. In this embodiment, the algorithm failed to detect portal vein in these two patients, so a manual detection of portal vein was relied upon. A better location of the PV will improve the accuracy of the algorithm.

2.3 Example C (PETAL)

In this example, called PETAL, 681 CT-scans (training: 479 CT-scans; validation: 202 CT-scans) from a multicenter clinical trial in patients with liver metastases from colorectal cancer were retrospectively analyzed for algorithm development and validation. An additional external validation was performed on a cohort of 228 CT-scans from gastrointestinal neuroendocrine cancer patients Image acquisition was performed according to each centers' standard CT with contrast protocol for single portal venous phase, portal venous acquisition. The reference gold standard for the classification of PVP-timing as either optimal or non-optimal was based on experienced radiologists' consensus opinion. The algorithm performed automated localization (on axial slices) of the portal vein and aorta upon which a novel dual input CNN calculated a probability of the optimal PVP-timing, which can be used to select an image and correct for any sub-optimal timing.

The algorithm automatically computed a PVP-timing score in 3 seconds and reached AUC of 0.837 (95% CI: 0.765, 0.890) in validation set and 0.844 (95% CI: 0.786, 0.889) in external validation set.

Thus, a fully automated, deep-learning derived PVP-timing algorithm was developed to classify scans' contrast enhancement timing and identify scans with optimal PVP-timing. The rapid identification of such scans will aid in the analysis of quantitative (radiomics) features used to characterize tumors and changes in enhancement with treatment in a multitude of settings including quantitative response criteria such as Choi and MASS which rely on reproducible measurement of enhancement.

Optimal PVP timing is crucial in oncology for the automatic detection and characterization of lesions, as well as the estimation of tumor enhancement or vascularity, which is increasingly being used to predict treatment response, as well as outcome and recurrence. In clinical trials and routine practice, anti-cancer treatment efficacy may be evaluated using response evaluation criteria in solid tumors (RECIST) or Choi criteria or MASS criteria or general assessment of tumor size and density. RECIST criteria define treatment response by tumor shrinkage, while Choi criteria specify that a 15% decrease in tumor density on CT-scan acquired at the PVP could be an additional surrogate marker of treatment efficacy. The incremental value of Choi criteria is in the detection of additional patients with clinical benefit, and the successful response rate can double (from 46% using RECIST to 83% using Choi criteria).

Previously, a visual assessment quality control (QC) tool, based on a three-point scoring system, was demonstrated to greatly improved the estimation of cancer drugs' efficacy using Choi criteria. The application of this QC for the evaluation of anticancer treatment efficacy demonstrated that a non-optimal PVP timing (too early or too late) significantly altered response evaluation when using the Choi criteria. A non-optimal PVP-timing induced an apparent, false 15% decrease in the measurement of tumor density. This study demonstrated the actual clinical utility of such QC tools. These previously designed QC tools used two different methodologies, both of which had limitations: (1) radiologists' visual assessment with a 3 point scale or (2) a semi-automatic classification software. The major limitation of the visual assessment is that it is highly reader dependent and subjective even after appropriate reader training. The ability to manually perform this type of QC depends on readers' skills and experience. Additionally, both visual assessment by a radiologist and the semi-automatic classification software can be time intensive due to the multitude of tasks that must be performed including optimizing viewing window width/level, and visually estimating density relationships between the relevant organs (or putting ROIs on the organs to calculate density ratios).

In this retrospective study, we selected liver metastasis from colorectal cancer (LM-CRC) to train and validate our PETAL algorithm, as colorectal cancer is the second leading cause of cancer death and liver metastasis involve greater than half of the patients with colorectal cancer. To study our algorithm's generalizability, we chose liver metastasis from gastrointestinal neuroendocrine tumors (LM-NET) as external validation dataset. The gastrointestinal NET is, indeed, the second most prevalent primary gastrointestinal malignancy. In the external validation dataset, we excluded patients with hepatectomy or any severe mass effect with portal vein anatomy changed. Both data sets were obtained from previous, already completed, multicenter clinical studies of colorectal and neuroendocrine tumors.

Patients' CT images were acquired with standard-of-care abdominal imaging protocols at the PVP after intravenous injection of an iodinated contrast-enhancement product. The PVP acquisition used fixed delay time after contrast injection. The CT imaging settings are shown in the supplemental materials Table 1.

TABLE 1

CT imaging settings statistics of LM-CRC and LM-NET dataset

| Dataset | Scanner | Tube voltage Mean ± SD | Tube current time Mean ± SD | Recon kernel | Slice thickness Mean ± SD | Pixel spacing Mean ± SD |
|---|---|---|---|---|---|---|
| LM-CRC | GE, Philips Siemens, etc | 121 ± 5 kVp | 180 ± 96 mAs | smooth | 4.9 ± 1.2 mm | 0.74 ± 0.09 mm |
| LM-NET | GE, Philips Siemens, etc | 122 ± 5 kVp | 172 ± 75 mAs | smooth | 3.5 ± 1.6 mm | 0.72 ± 0.09 mm |

We randomly divided LM-CRC dataset into training and validation sets on a ratio of 7:3 for the deep learning algorithm development. CT-scans from the same patients were assigned to the same group: assigned either to the training set or to the validation set. In total, 479 PVP CT-scans (300 optimal and 179 non-optimal) from LM-CRC dataset were used for training and 202 PVP CT-scans (137 optimal and 65 non-optimal) from LM-CRC dataset were used for validation. The external validation set utilized LM-NET dataset with 228 PVP CT-scans (111 optimal and 117 non-optimal).

For each CT-scan, two out of five radiologists with 3, 5, 8, 12, and 15 years of experience independently classified the scans' timing as optimal or non-optimal PVP. The reference standard was the three-phase consensus process as follows. We categorized the PVP timing as optimal or non-optimal. Nonoptimal PVP timing included either early or late PVP timing. The definition was based on the relative contrast enhancement within vessels and tissues. Optimal PVP demonstrated peak enhancement of the liver parenchyma and portal vein, as well as some enhancement of the hepatic veins. Early PVP was defined by contrast still predominantly in the arterial supply as compared with the portal vein. Late PVP was associated with a washout of the hepatic contrast enhancement and approached the nephrogenic phase with more enhancement of the renal medulla.

(1) Initial Visual Consensus. CT scans were divided (randomly) and scored by pairs of trained radiologists. The radiologists independently read their CT scans and scored the PVP timing. If the two radiologists' scores agreed, then the score was finalized. If the two radiologists disagreed, then a joint consensus reading was performed between both radiologists after a time interval to avoid memory bias. If the two radiologists from one pair could not reach an agreement during the consensus reading, then a third radiologist, from the other pair, adjudicated to reach a majority consensus for the score.

(2) Semi-automatic classification. We used a previously described semi-automatic classification of PVP timing to ensure the quality and reproducibility of our PVP timing classification. To this end, we used a previously described probability map that the PVP timing was optimal based on the measurement of the density in Hounsfield Unit of the portal vein and of the aorta.

(3) Final (including 1 and 2) Reference standard Consensus. For any semi-automatic classification that differed from the initial visual consensus, an additional consensus reading was performed by the pair of radiologists to determine the optimal PVP timing classification. The goal was to obtain the most accurate and optimal reference-standard PVP-timing consensus for subsequent analyses. In summary, this was derived from (1) a visual consensus between a pair or trio of radiologists, (2) a computer-aided detection of potentially misclassified scans, and (3) a final visual consensus by the radiologists for any misclassified scan.

The contrast enhancement in portal vein and aorta was demonstrated to be the dominant information that contributed to classify the optimal PVP-timing as the ROIs in liver, spleen, inferior vena cava, psoas muscle, and kidney did not provide incremental value. With this knowledge, an automated algorithm for deriving a probability of optimal PVP-timing by analyzing the portal vein and aorta was developed with the 6 steps outlined above with reference to FIG. 3A.

The new dual CNN, described above with reference to FIG. 4, was developed to process the image patches of the portal vein and aorta at the same time. In this network, two blocks of two consecutive convolutional layers with 32 and 64 filters were used. Each filter had 3-by-3 pixels convolutional kernels with ReLU activation, zero padding on the edge. Each block was followed by a 2-by-2 max-pooling layer and a dropout layer of dropout-rate 50%. Finally, the fully connected layer of 512 nodes combined the information about the portal vein and the aorta. The final 1 node layer was connected with the previous layers with sigmoid activation. We trained the network through a training set of 479 CT images by using stochastic gradient descent optimizer with the momentum—of 0.9, 128 mini batch size, 100 epochs, and 0.01 learning rate.

We performed deep learning with a GTX 1060 GPU (NVIDIA, Santa Clara, Calif.) and an Intel i7-7700HQ 2.8 GHz CPU (Intel, Santa Clara, Calif.). Python 3.6 and Matlab 2017b were used for programming.

The dual CNN can obtain each score analyzing each pair of portal vein bounding-box and aorta bounding-box. The score is a value between zero and one indicating the probability of optimal timing. Five pairs of portal vein and aorta resulted in five scores. The final PVP score was the average of these five scores.

We used Free-Response ROC (FROC) to evaluate the detection performance of the portal vein and aorta. The performance of PETAL was evaluated in terms of AUC of ROC curve. The 95% confidence interval of AUC was estimated by using bootstrapping with 1000 bootstraps of prediction scores. We collected two cohorts of data independently. The LM-CRC cohort was used for training and validating PETAL and the LM-NET was used for testing PETAL blindly.

Portal vein slices classification. In the external validation set, four cases failed to locate the axial slices containing portal vein (1.75%) due to poor contrast in the PV (n=1), displaced portal vein caused by mass effect (n=2) and systematic failure of the algorithm (n=1, contrast enhancement was unexpectedly high in the PV with 360 HU, which is above our abdominal CT window of −160~240 HU). Portal vein detection PETAL algorithm extracted totally 1,046 bounding-boxes of portal veins from 228 cases in the external validation set and received 90.6% sensitivity with one false positive per scan. One radiologist analyzed the detections of 1,046 bounding boxes visually. There were some errors due to selection of multiple vessels (especially in the coeliac trunk 93 cases, 8.9%), detections of bone vertebra or rib (71 cases, 6.8%), detection of structures with oral contrast enhancement (opacification digestive tract, 18 cases, 1.7%), and selection of normal structures such as liver, kidney, stomach (65 case, 6.2%).

Aorta detection. The aorta detection was almost perfect; it achieved 100% sensitivity with 0.0134 false positives per scan. We analyzed the detections of all 1,046 bounding-boxes in the external validation set. There were three mistakes out of 1,046 cases, two of which were caused by oral contrast enhancement and one was caused by selection of multiple vessels in the coeliac trunk.

PVP classification. The PVP probability of PETAL outputs ranged from 0 to 1. In the external validation set, the optimal threshold of the PVP probability was 0.84. The corresponding sensitivity at this operating point was 82% and the specificity was 74%. The positive predictive value was 75% and the negative predictive value was 81% at the same operating point. The AUC value of the validation set is 0.837 (95% CI: 0.765, 0.890) and of the external validation set is 0.844 (95% CI: 0.786, 0.889). The performance was good (0.837 AUC) on the LM-CRC dataset from which PETAL was developed. Besides, the performance was also good (0.844 AUC) on the LM-NET dataset that was different tumor type from the training set.

Duration of data processing. PETAL algorithm can evaluate a CT scan in 3 seconds on average by a computer with a GTX 1060 GPU and an Intel i7-7700HQ 2.8 GHz CPU. The algorithm was fully automatic and was perfectly reproducible when reapplied to the same dataset.

The performance of the algorithm was comparable with the radiologists for the visual assessment of the PVP timing, which was reported to be 81.7% accuracy in [14]. It achieved an AUC of 0.837 (95% CI: 0.765, 0.890) in the validation set and an AUC of 0.844 (95% CI: 0.786, 0.889) in the external validation set. Thus, the deep learning method was able to differentiate an optimal PVP-timing vs. a non-optimal PVP-timing (early or late PVP) acquisition.

There are a number of applications for this type of technology especially in comparative imaging studies obtained temporally. We are exploring its use in radiomic analysis of lesions in the abdomen. An advantage is the ability to use this technology in prospective analyses as well as to exclude non-optimal PVP acquisitions on retrospective studies.

By automatically monitoring PVP timing and potentially excluding imaging data sets with improper acquisition timing, this algorithm may help to ensure an optimal extraction of imaging biomarkers that could be useful to classify new patterns of progression and response in novel anticancer agents. It could also be applied to improve radiomics signatures by selecting CT images of optimal quality. The algorithm is capable of ensuring that conditions are optimal to appraise tumor vascularity and density-based response criteria such as CHOI. A previous study demonstrated that a 14.8% variability in tumor density measurement was directly caused by variation in PVP acquisition timing which is deleterious to the use of density as a biomarker, because tumor density reduction would not be robust as its variability could be due to acquisition timing (rather than tumor lesion biology) and would therefore be poor at predicting overall survival and progression-free survival. Increasing the reproducibility of tumor density measurements is essential to acceptance of density-based biomarkers as the basis for imaging endpoints in clinical trials and response in new anticancer agents.

This algorithm potentially provides additional and incremental value to the current bolus tracking technique used in CT imaging Bolus tracking is used during the imaging acquisition to control phase timing so that the likelihood of the PVP-timing being optimal is increased. However, it does not consider the individual patient's biological variation and thus cannot ensure if the optimal PVP-timing was successfully reached in a given patient. In bolus tracking, a small bolus of radio-opaque contrast media is injected into a patient via a peripheral intravenous cannula. The flow of contrast to a specific vessel can be tracked using an ROI. When the contrast in the vessel reaches a certain threshold, the acquisition timing is considered optimal and triggers the CT-scan acquisition. Additionally, bolus tracking is not used in all center and most centers still rely on image acquisition on the historical and empirical 60-second delay between contrast agent product injection and image acquisitions. The problem is that the individual optimal hepatic enhancement timing cannot be assumed a priori, because it is associated with multiple variables as well as the anthropomorphic characteristics and hemodynamic status of the patient. Consequently, an optimal PVP timing is only reached in two out of three patients in multicenter clinical trials. Hence, the need for such quality control techniques is critical.

In conclusion, our work demonstrates that a fully automatic, deep-learning derived PVP-timing recognition system can reliably, reproducibly and rapidly identify the optimal PVP-timing based on CT images. This technique could be invaluable for any type of image analysis, such as radiomics, which rely on features that might be affected by the phase of contrast administration and scanning.

2.4 Example D—Use of Three Post Contrast Phases

In this embodiment, we aimed to determine whether there was sufficient information content in at least some applications to support the use of three post contrast phases represented by three output nodes in the output layer 280 indicating the probability of pre optimal (before peak contrast), optimal (during peak contrast) and post optimal (after peak contrast).

To this end, we investigated the reproducibility of the measurement of tumor density at the arterial phase in Hepatocellular carcinoma (HCC) by developing and validating a semi-automatic arterial-timing random forest classification algorithm based on the analysis of the pharmacokinetic distribution of the iodinated contrast agent a single timepoint (ACACIAS).

Using dynamic CT-images of 69 HCC patients (pts), we trained (48 pts, 1930 timepoints) and validated (21 pts, 837 timepoints). ACACIAS categorizes arterial-timing into five phases according to the time to arterial peak: early (E0)<−15 s<pre-peak (Pre1)<−5 s<peak (P2)<+5 s<post-peak (Post3) <+15 s<late (L4). The random forest algorithm was used to quickly build a model based on the average density in predefined ROIs. Using an independent testing set, we delineated and calculated the average density of biopsy-proven HCC in 90 pts with cirrhotic liver at three phases: non-contrast enhanced 'NCP (e.g., pre peak)', arterial 'AP' (near peak) and portal 'PVP (post peak)'. These were highly correlated with the ACACIAS categories.

In the validation set, ACACIAS predicted correctly phases E0, Pre1, P2, Post3, and L4 in respectively 92%, 58%, 86%, 30%, and 99% of pts. Inter-patient variability in the duration of the arterial peak (5-95th percentiles of Full Width at Half Maximum: 10.6-27.5 s) explained lower accuracies of ACACIAS in Pre1 and Post3 phases. In the testing set, 96% of NCP and 97% of PVP were correctly classified. The predicted arterial timing of AP for E0, Pre1, P2, Post3, and L4 was respectively 1, 34, 13, 25, and 17 pts and was associated with a significant difference in mean tumor density: 68, 55, 60, 71, and 60 HU. The arterial HCC enhancement peaked at phase Post3 (+17%), (P<0.02, ANOVA). Thus, there was sufficient support for deducing one of three post contrast phases in a single slice.

We conclude that ACACIAS predicted arterial timing accurately based on iodine biodistribution on medical images. A peak of HCC tumor density (+17%) was observed at the arterial phase 'Post3'. ACACIAS could improve extraction of tumor quantitative imaging biomarkers and monitoring of anti-cancer therapy efficacy by ensuring reproducible arterial phase acquisitions.

The clinical relevance/application of ACACIAS is that it ensures a reproducible tumor density measurement at arterial phase for treatment response assessment, as well as wide-ranging applications since tumor density is a surrogate of vascularity.

Based on the success of ACACIAS, it is evident that three post contrast phases can be deduced from the amplitudes in the artery and portal vein image regions.

2.5 Example E—Use of Five Post Contrast Phases

In this embodiment, we aimed to determine whether there was sufficient information content in at least some applications to support the use of five post contrast phases represented by five output nodes in the output layer 280, indicating the probability of the following five phases, namely: non-contrast (NCP); early arterial phase (EAP); optimal arterial phase (OAP); optimal portal venous phase (OPVP); and, late portal venous phase (LPVP).

To this end, we developed a novel Contrast-Enhancement CT-scan Quality Control (CECT-QC) algorithm to provide improved standardization and quality control in the evaluation of contrast-enhancement quality. Using random forest machine-learning, the CECT-QC algorithm was trained to identify the optimal contrast-enhancement phases of abdominal CT scan images and was successful in determining five different phases.

The CECT-QC algorithm was developed in patients with hepatocellular carcinoma (HCC). HCC is the most common primary hepatic malignancy and the fourth leading cause of cancer-related deaths worldwide. The CECT-QC algorithm was investigated using cirrhotic patients as the target patient population since cirrhosis, the main risk factor for developing HCC, alters the biodistribution of contrast-enhancement product in all tissues. Pathophysiology of cirrhosis as well as cirrhotic cardiomyopathy can significantly alter the extraction of imaging biomarkers in HCC tissues by altering the biodistribution of the contrast-enhancement product and delay or decrease portal vein enhancement. Therefore, optimal liver contrast-enhancement is challenging in cirrhotic patients.

Multicenter data from four independent cohorts [A, B, C, D] totaling 503 patients with measurable liver lesions evaluated at 3397 time-points were analyzed retrospectively: [A] dynamic CTs from 60 patients with primary liver cancer (2359 time-points); [B] triphasic CTs from 31 cirrhotic patients with primary liver cancer (93 time-points); [C] triphasic CTs from 121 cirrhotic patients with hepatocellular carcinoma (363 time-points); [D] 291 patients with liver metastasis from colorectal cancer at the PVP (2 acquisitions for each patient, 582 time-points). Patients from cohort A, were randomized to training-set and test-set (48:12 patients, 1884:475 time-points).

In the first part of this study, we trained and tested a phase classifier, i.e., the CECT-QC algorithm, using a machine-learning method in cohort A. The input was the contrast-enhancement density in aorta and portal vein. The reference standard and output to be predicted was a time interval spanned by five clinically utilized contrast-enhancement phases The acquisition times of the dynamic CT-scan images were continuous variables that we transformed into a discrete categorization over 5 phases: (i) Non-contrast [NCP]; (ii) Early Arterial [E-AP]; (iii) Optimal Arterial [O-AP]; (iv) Optimal Portal Venous [O-PVP]; (v) Late Portal Venous [L-PVP]. At each time-point the original time values (i.e., the time after contrast injection provided in the image Digital Imaging and Communications in Medicine DICOM header) were replaced by a single discrete value (i.e., 1-5) representative of a time interval spanned by the 5 phases.

As a surrogate for the neural network classifier, a random forest classifier was trained to classify each conventional CT image acquired at a single time point into one of the 5 phases. During the training, each time-point from one patient was treated as an independent time-point. The random forest classifier utilized ten trees with a maximum growing depth of five (22). The output of the classifier was one of the 5 phases. The input of the phase classifier was the mean density of the abdominal aorta and the portal vein measured from each time point/image to be classified because they were shown to be the two most informative locations for predicting the contrast-enhancement phase.

Figure 5:
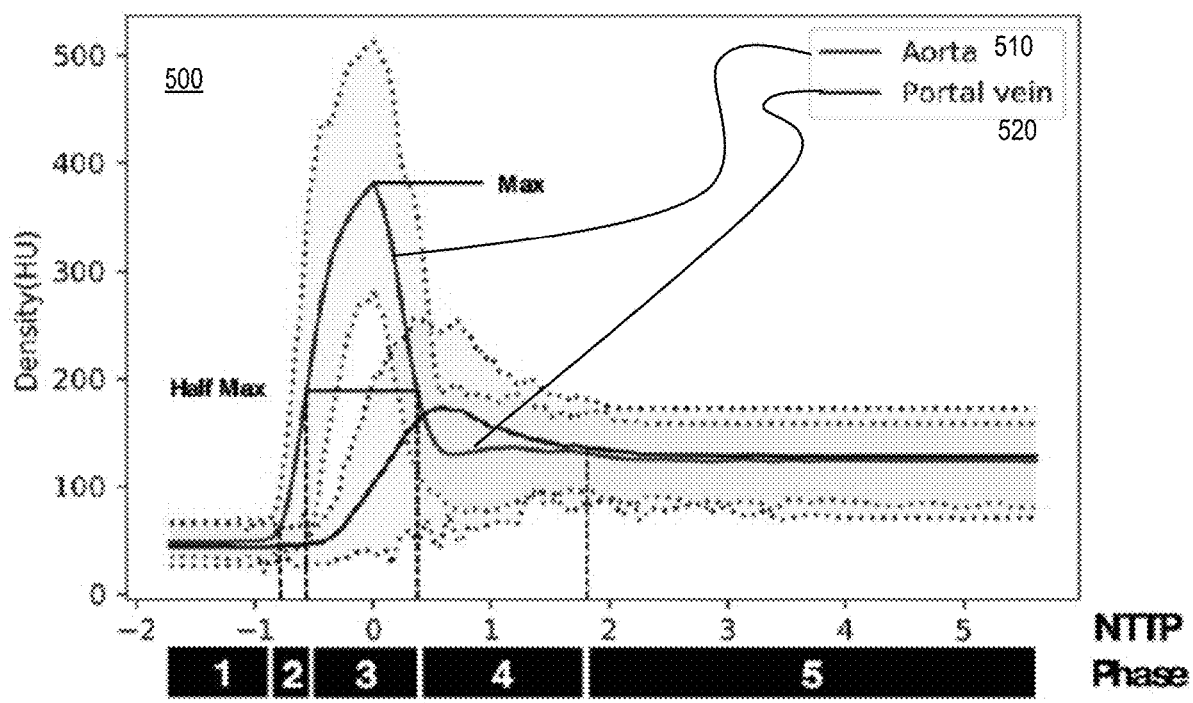
FIG. 5 is a graph that illustrates example time evolution of amplitude in the aorta and portal venous image regions, utilized according to an embodiment.

FIG. 5 is a graph 500 that illustrates example time evolution of amplitude in the aorta and portal venous image regions, utilized according to an embodiment. The horizontal axis indicates time in minutes and the vertical axis indicates density (average amplitude within the image region defined as an anatomic feature in HU. Trace 510 indicates average density in the aorta at each time and the surrounding envelope indicates the spread of density among patients. Trace 520 indicates average density in the porta venous at each time and the surrounding envelope indicates the spread of density among patients. There was a significant inter-patient variability in contrast-enhancement biodistribution kinetics. Using this information, a discrete classification into 5 phases was performed for all patients, labeling the time axis with intervals 1 through 5 for the 5 phases, respectively.

Figure 6:
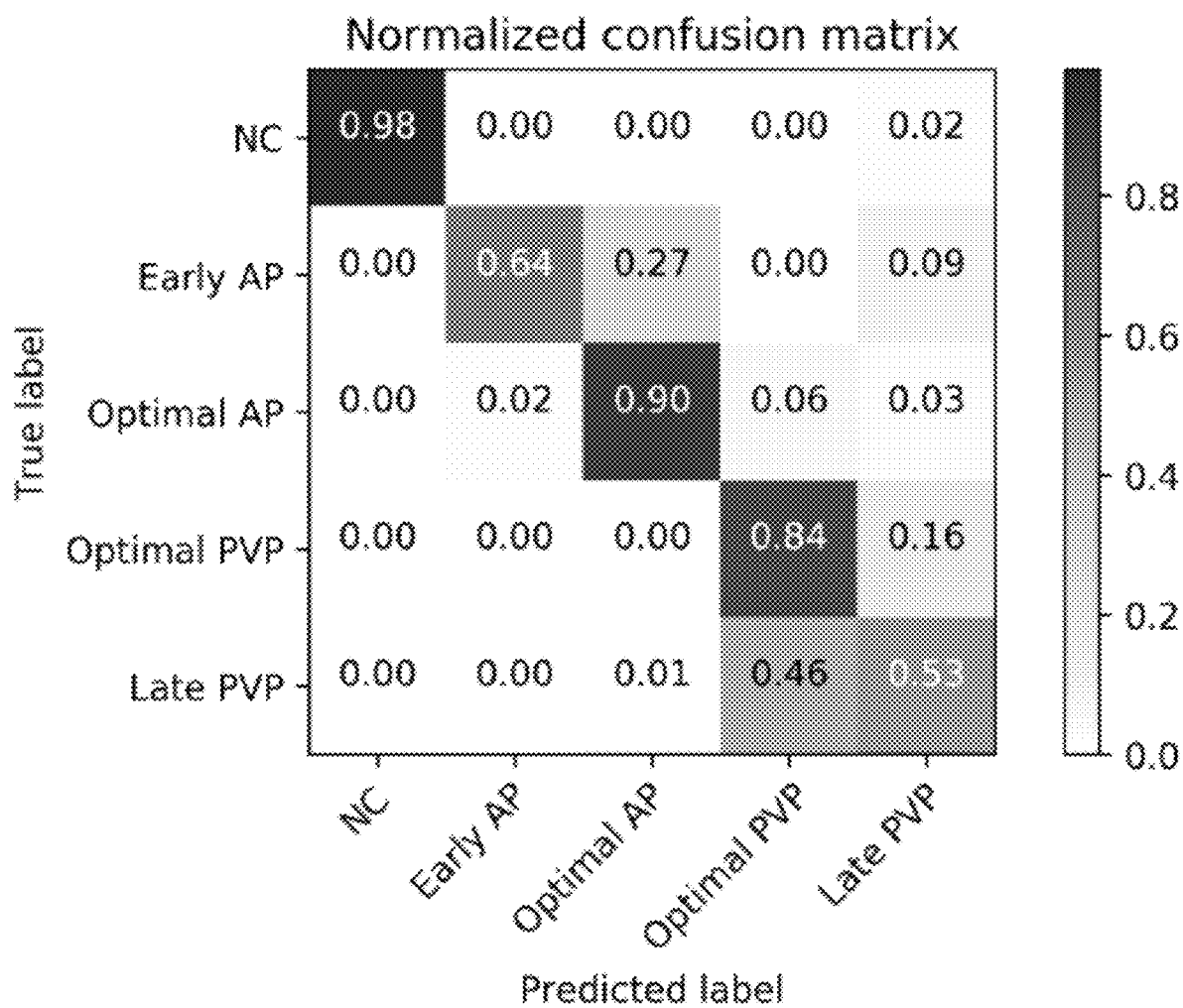
FIG. 6 is a table that illustrates an example confusion matrix between actual and predicted phases, utilized according to an embodiment.

The accuracy of the developed CECT-QC algorithm was evaluated against the test-set. The performance was calculated using 95% confidence intervals [95% CIs] using 1000-bootstrap. A normalized confusion matrix displays the comparison of the predicted phase using the classifier to the reference standard phase. FIG. 6 is a table that illustrates an example confusion matrix between actual and predicted phases, utilized according to an embodiment. The CE phase can be predicted by machine-learning with good accuracy.

Performance of the CECT-QC algorithm was evaluated in the test-set. The CECT-QC algorithm reached an overall accuracy of 79.4% [95% CI=75.2%, 82.9%] (377 correct predictions out of 475 total predictions) to predict the phase based on the analysis of a single image at a single time point. As shown in FIG. 6, the accuracies to detect optimal acquisition phases were 98% for NCP, 90% for O-AP, and 84% for O-PVP.

The distinction in phase is clinically significant. For example, the liver metastasis density (mean±SD in HU) peaked at optimal-PVP (61±14 HU). Moreover, optimal PVP showed increases of 20% and 18% in tumor density compared to optimal-AP and late-PVP respectively.

In conclusion, the CECT-QC algorithm developed in this study was trained and validated in a large dataset of 503 patients and 3397 time-points. It offers a proof of concept that machine-learning, applied to a single image using two simple anatomical landmarks, allows an accurate categorization of five contrast-enhancement phases. Using this quality control tool can help to improve the reproducibility of tumor imaging biomarker extraction for radiomic-based precision diagnosis and treatment in liver diseases, both at patient and clinical trial level.

3. COMPUTATIONAL HARDWARE OVERVIEW

Figure 7:
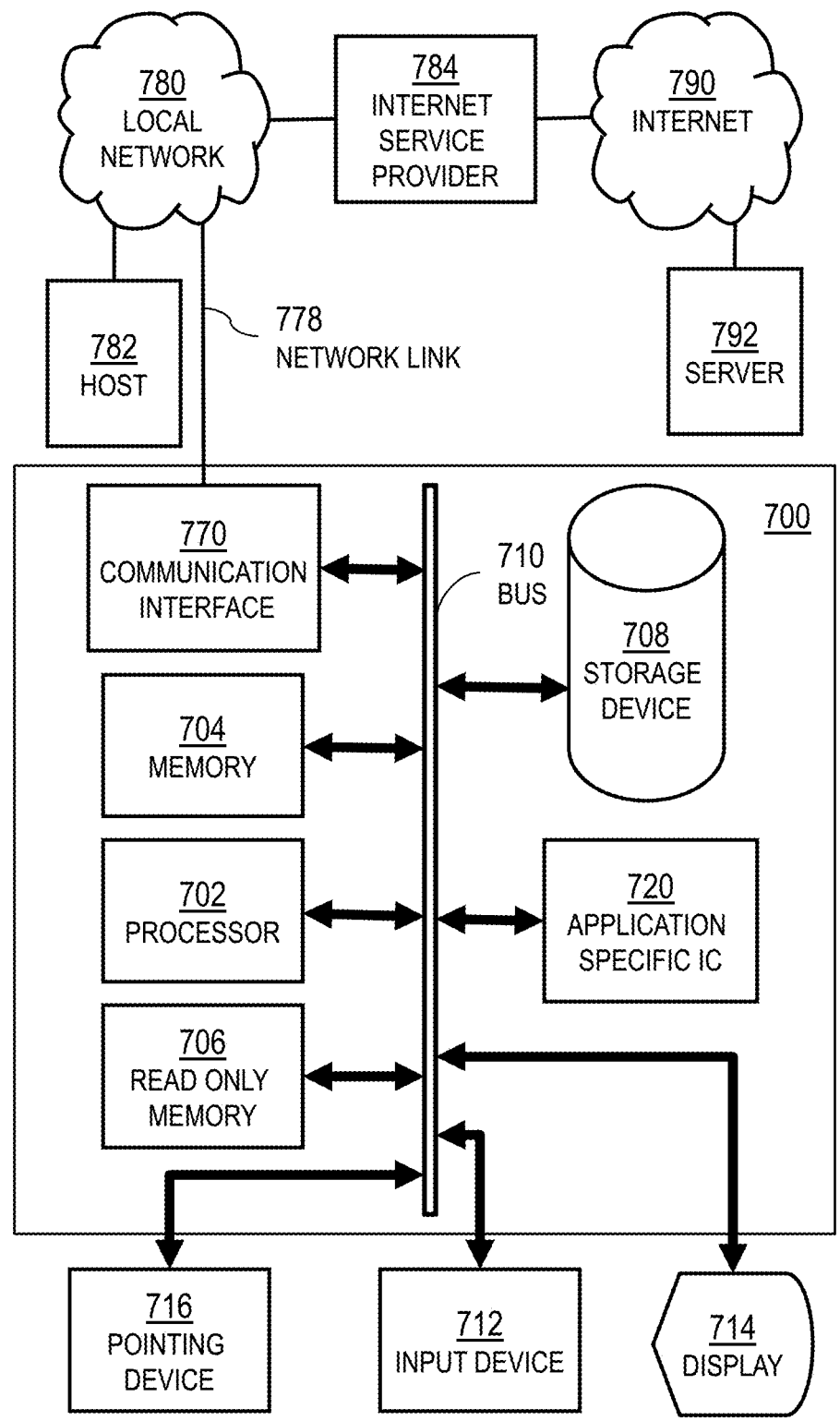
FIG. 7 is a block diagram that illustrates a computer system upon which an embodiment of the invention may be implemented.

FIG. 7 is a block diagram that illustrates a computer system 700 upon which an embodiment of the invention may be implemented. Computer system 700 includes a communication mechanism such as a bus 710 for passing information between other internal and external components of the computer system 700. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit)). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 700, or a portion thereof, constitutes a means for performing one or more steps of one or more methods described herein.

A sequence of binary digits constitutes digital data that is used to represent a number or code for a character. A bus 710 includes many parallel conductors of information so that information is transferred quickly among devices coupled to the bus 710. One or more processors 702 for processing information are coupled with the bus 710. A processor 702 performs a set of operations on information. The set of operations include bringing information in from the bus 710 and placing information on the bus 710. The set of operations also typically include comparing two or more units of information, shifting positions of units of information, and combining two or more units of information, such as by addition or multiplication. A sequence of operations to be executed by the processor 702 constitutes computer instructions.

Computer system 700 also includes a memory 704 coupled to bus 710. The memory 704, such as a random access memory (RAM) or other dynamic storage device, stores information including computer instructions. Dynamic memory allows information stored therein to be changed by the computer system 700. RAM allows a unit of information stored at a location called a memory address to be stored and retrieved independently of information at neighboring addresses. The memory 704 is also used by the processor 702 to store temporary values during execution of computer instructions. The computer system 700 also includes a read only memory (ROM) 706 or other static storage device coupled to the bus 710 for storing static information, including instructions, that is not changed by the computer system 700. Also coupled to bus 710 is a non-volatile (persistent) storage device 708, such as a magnetic disk or optical disk, for storing information, including instructions, that persists even when the computer system 700 is turned off or otherwise loses power.

Information, including instructions, is provided to the bus 710 for use by the processor from an external input device 712, such as a keyboard containing alphanumeric keys operated by a human user, or a sensor. A sensor detects conditions in its vicinity and transforms those detections into signals compatible with the signals used to represent information in computer system 700. Other external devices coupled to bus 710, used primarily for interacting with humans, include a display device 714, such as a cathode ray tube (CRT) or a liquid crystal display (LCD), for presenting images, and a pointing device 716, such as a mouse or a trackball or cursor direction keys, for controlling a position of a small cursor image presented on the display 714 and issuing commands associated with graphical elements presented on the display 714.

In the illustrated embodiment, special purpose hardware, such as an application specific integrated circuit (IC) 720, is coupled to bus 710. The special purpose hardware is configured to perform operations not performed by processor 702 quickly enough for special purposes. Examples of application specific ICs include graphics accelerator cards for generating images for display 714, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 700 also includes one or more instances of a communications interface 770 coupled to bus 710. Communication interface 770 provides a two-way communication coupling to a variety of external devices that operate with their own processors, such as printers, scanners and external disks. In general the coupling is with a network link 778 that is connected to a local network 780 to which a variety of external devices with their own processors are connected. For example, communication interface 770 may be a parallel port or a serial port or a universal serial bus (USB) port on a personal computer. In some embodiments, communications interface 770 is an integrated services digital network (ISDN) card or a digital subscriber line (DSL) card or a telephone modem that provides an information communication connection to a corresponding type of telephone line. In some embodiments, a communication interface 770 is a cable modem that converts signals on bus 710 into signals for a communication connection over a coaxial cable or into optical signals for a communication connection over a fiber optic cable. As another example, communications interface 770 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 770 sends and receives electrical, acoustic or electromagnetic signals, including infrared and optical signals, that carry information streams, such as digital data.

The term computer-readable medium is used herein to refer to any medium that participates in providing information to processor 702, including instructions for execution. Such a medium may take many forms, including, but not limited to, non-volatile media, volatile media and transmission media. Non-volatile media include, for example, optical or magnetic disks, such as storage device 708. Volatile media include, for example, dynamic memory 704. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 702, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 702, except for carrier waves and other signals.

Logic encoded in one or more tangible media includes one or both of processor instructions on a computer-readable storage media and special purpose hardware, such as ASIC 720.

Network link 778 typically provides information communication through one or more networks to other devices that use or process the information. For example, network link 778 may provide a connection through local network 780 to a host computer 782 or to equipment 784 operated by an Internet Service Provider (ISP). ISP equipment 784 in turn provides data communication services through the public, world-wide packet-switching communication network of networks now commonly referred to as the Internet 790. A computer called a server 792 connected to the Internet provides a service in response to information received over the Internet. For example, server 792 provides information representing video data for presentation at display 714.

The invention is related to the use of computer system 700 for implementing the techniques described herein. According to one embodiment of the invention, those techniques are performed by computer system 700 in response to processor 702 executing one or more sequences of one or more instructions contained in memory 704. Such instructions, also called software and program code, may be read into memory 704 from another computer-readable medium such as storage device 708. Execution of the sequences of instructions contained in memory 704 causes processor 702 to perform the method steps described herein. In alternative embodiments, hardware, such as application specific integrated circuit 720, may be used in place of or in combination with software to implement the invention. Thus, embodiments of the invention are not limited to any specific combination of hardware and software.

The signals transmitted over network link 778 and other networks through communications interface 770, carry information to and from computer system 700. Computer system 700 can send and receive information, including program code, through the networks 780, 790 among others, through network link 778 and communications interface 770. In an example using the Internet 790, a server 792 transmits program code for a particular application, requested by a message sent from computer 700, through Internet 790, ISP equipment 784, local network 780 and communications interface 770. The received code may be executed by processor 702 as it is received, or may be stored in storage device 708 or other non-volatile storage for later execution, or both. In this manner, computer system 700 may obtain application program code in the form of a signal on a carrier wave.

Various forms of computer readable media may be involved in carrying one or more sequence of instructions or data or both to processor 702 for execution. For example, instructions and data may initially be carried on a magnetic disk of a remote computer such as host 782. The remote computer loads the instructions and data into its dynamic memory and sends the instructions and data over a telephone line using a modem. A modem local to the computer system 700 receives the instructions and data on a telephone line and uses an infra-red transmitter to convert the instructions and data to a signal on an infra-red a carrier wave serving as the network link 778. An infrared detector serving as communications interface 770 receives the instructions and data carried in the infrared signal and places information representing the instructions and data onto bus 710. Bus 710 carries the information to memory 704 from which processor 702 retrieves and executes the instructions using some of the data sent with the instructions. The instructions and data received in memory 704 may optionally be stored on storage device 708, either before or after execution by the processor 702.

Figure 8:
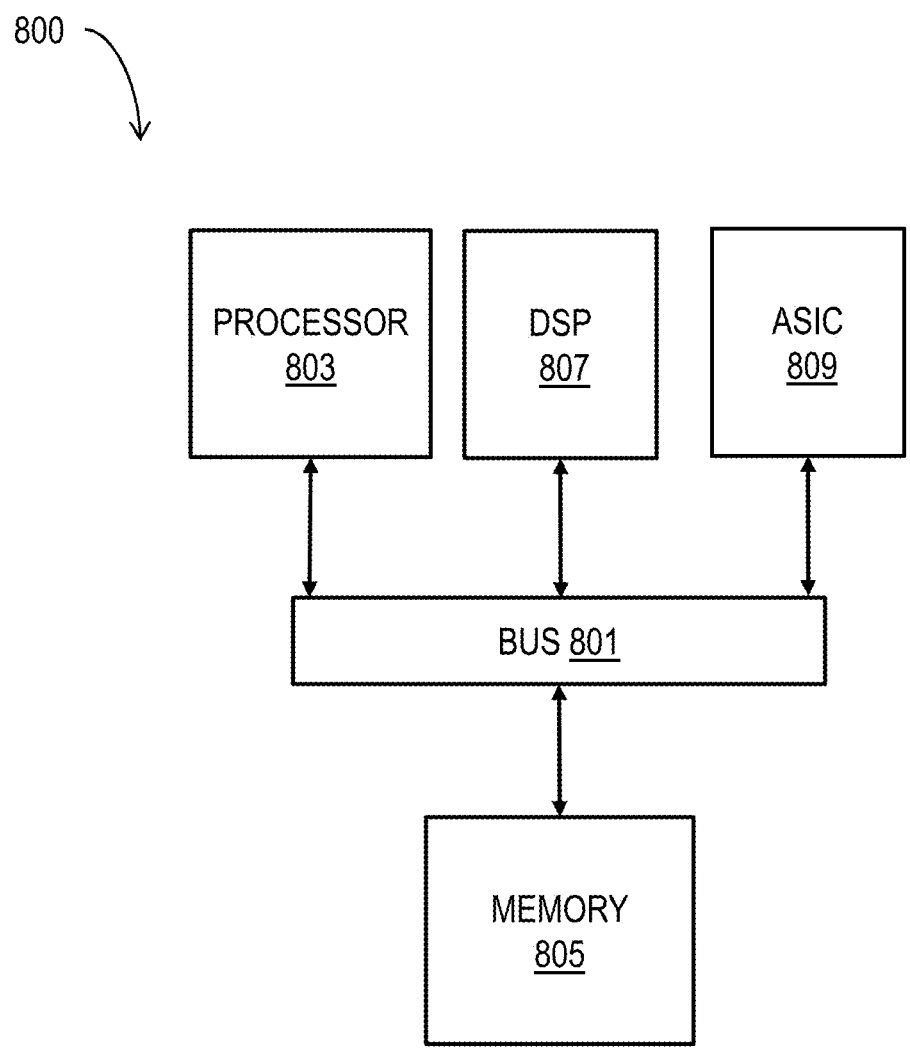
FIG. 8 illustrates a chip set upon which an embodiment of the invention may be implemented.

FIG. 8 illustrates a chip set 800 upon which an embodiment of the invention may be implemented. Chip set 800 is programmed to perform one or more steps of a method described herein and includes, for instance, the processor and memory components described with respect to FIG. 7 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 800, or a portion thereof, constitutes a means for performing one or more steps of a method described herein.

In one embodiment, the chip set 800 includes a communication mechanism such as a bus 801 for passing information among the components of the chip set 800. A processor 803 has connectivity to the bus 801 to execute instructions and process information stored in, for example, a memory 805. The processor 803 may include one or more processing cores with each core configured to perform independently. A multi-core processor enables multiprocessing within a single physical package. Examples of a multi-core processor include two, four, eight, or greater numbers of processing cores. Alternatively or in addition, the processor 803 may include one or more microprocessors configured in tandem via the bus 801 to enable independent execution of instructions, pipelining, and multithreading. The processor 803 may also be accompanied with one or more specialized components to perform certain processing functions and tasks such as one or more digital signal processors (DSP) 807, or one or more application-specific integrated circuits (ASIC) 809. A DSP 807 typically is configured to process real-world signals (e.g., sound) in real time independently of the processor 803. Similarly, an ASIC 809 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 803 and accompanying components have connectivity to the memory 805 via the bus 801. The memory 805 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 805 also stores the data associated with or generated by the execution of one or more steps of the methods described herein.

3. ALTERNATIVES, DEVIATIONS AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

4. REFERENCES

The references cited here and in the Appendices are each incorporated by reference as if fully contained herein, except for terminology that is inconsistent with that used herein.

Huang, Q., Dercle, L., Lu, L., Lichtenstein, P., Zhu, J., Wang, D., Schwartz, L. H., Zhao, B., "Automated Contrast Timing Classification with Deep Convolutional Neural Networks," Published in Radiological Society of North America 2017 Scientific Assembly and Annual Meeting, Nov. 27-Dec. 2, 2017, Chicago IL.

What is claimed is:

1. A method for measuring post contrast phase, comprising:
    collecting three dimensional (3D) medical imagery of a subject using a 3D medical imaging device after injecting the subject with a contrast agent;
    selecting a first set of one or more slices displaced in the axial direction, wherein each slice in the set includes a first anatomical feature selected from a group consisting of an aorta, a portal vein, an inferior vena cava, a liver, a spleen and a renal cortex;
    selecting a second set of one or more slices displaced in the axial direction, wherein each slice in the second set includes a different second anatomical feature selected from the group;
    selecting a first image region on a first slice of the first set and a different second image region on a second slice of the second set, wherein the first image region includes the first anatomical feature and the second image region includes the different second anatomical feature;
    using a first trained convolutional neural network on a processor with input based on the first image region and the second image region, determining automatically on the processor a post contrast phase, wherein the first trained neural network comprises:
a first plurality of convolutional hidden layers operating on the first image region;
a second plurality of convolutional hidden layers operating on the second image region; and
at least one fully connected hidden layer receiving output from both the first plurality of convolutional hidden layers and the second plurality of convolutional hidden layers, and outputting to an output layer of one or more nodes corresponding values that each represent a probability of a post contrast phase; and
presenting automatically, on a display device, output data based on the post contrast phase.

2. The method as recited in claim 1, wherein:
said selecting the first image region is performed automatically on the processor using a second trained convolutional neural network with first input based on a set of one or more contiguous slices the 3D medial imagery;
said selecting the second image region is performed automatically on the processor using a different third trained convolutional neural network with second input based on the set of one or more contiguous slices the 3D medial imagery.

3. The method as recited in claim 2, further comprising determining the first set of one or more contiguous slices automatically on the processor using a different fourth trained convolutional neural network with first input based on the 3D medial imagery and output that indicates a probability that each slice includes the first anatomical feature.

4. The method as recited in claim 1, wherein the output data comprises an image of vascular density.

5. The method as recited in claim 1, wherein the output data comprises a set of output images displaced in the axial direction of vascular density.

6. The method as recited in claim 1, wherein the output data comprises a set of output images displaced in the axial direction of a tumor density or a tumor boundary.

7. The method as recited in claim 1, wherein the output data indicates a tumor density or a tumor boundary.

8. A non-transitory computer-readable medium carrying one or more sequences of instructions for measuring post contrast phase, wherein execution of the one or more sequences of instructions by one or more processors causes the one or more processors to perform at least the following:
collect three dimensional (3D) medical imagery of a subject using a 3D medical imaging device after the subject is injected with a contrast agent;
obtain a first set of one or more slices displaced in the axial direction, wherein each slice in the set includes a first anatomical feature selected from a group consisting of an aorta, a portal vein, an inferior vena cava, a liver, a spleen and a renal cortex;
obtain a second set of one or more slices displaced in the axial direction, wherein each slice in the second set includes a different second anatomical feature selected from the group;
obtain a first image region on a first slice of the first set and a different second image region on a second slice of the second set, wherein the first image region includes the first anatomical feature and the second image region includes the different second anatomical feature;
use a first trained convolutional neural network with input based on the first image region and the second image region, configured to determine a post contrast phase, wherein the first trained neural network comprises:
a first plurality of convolutional hidden layers operating on the first image region;
a second plurality of convolutional hidden layers operating on the second image region; and
at least one fully connected hidden layer receiving output from both the first plurality of convolutional hidden layers and the second plurality of convolutional hidden layers, and outputting to an output layer of one or more nodes corresponding values each representing a probability of a post contrast phase; and
present automatically, on a display device, output data based on the post contrast phase.

9. The computer-readable medium as recited in claim 8, wherein:
to obtain the first image region is performed using a second trained convolutional neural network with first input based on a set of one or more contiguous slices the 3D medial imagery;
to obtain the second image region is performed using a different third trained convolutional neural network with second input based on the set of one or more contiguous slices the 3D medial imagery.

10. The computer-readable medium as recited in claim 9, wherein execution of the one or more sequences of instructions further causes the one or more processors to determine the first set of one or more contiguous slices automatically on the processor using a different fourth trained convolutional neural network with first input based on the 3D medial imagery and output that indicates a probability that each slice includes the first anatomical feature.

11. The computer-readable medium as recited in claim 8, wherein the output data comprises an image of vascular density.

12. The computer-readable medium as recited in claim 8, wherein the output data comprises a set of output images displaced in the axial direction of vascular density.

13. The computer-readable medium as recited in claim 8, wherein the output data comprises a set of output images displaced in the axial direction of a tumor density or a tumor boundary.

14. The computer-readable medium as recited in claim 8, wherein the output data a tumor density or a tumor boundary.

15. A system for measuring post contrast phase comprising:
a three dimensional (3D) medical imaging device;
a display device;
at least one processor; and
at least one memory including one or more sequences of instructions,
the at least one memory and the one or more sequences of instructions configured to, with the at least one processor, cause the apparatus to perform at least the following,
collect 3D medical imagery of a subject using the 3D medical imaging device after the subject is injected with a contrast agent;
obtain a first set of one or more slices displaced in the axial direction, wherein each slice in the first set includes a first anatomical feature selected from a group consisting of an aorta, a portal vein, an inferior vena cava, a liver, a spleen and a renal cortex;

obtain a second set of one or more slices displaced in the axial direction, wherein each slice in the second set includes a different second anatomical feature selected from the group; obtain a first image region on a first slice of the first set and a second image region on a second slice of the second set, wherein the first image region includes the first anatomical feature and the second image region includes the different second anatomical feature;

use a first trained convolutional neural network with input based on the first image region and the second image region, configured for determining a post contrast phase, wherein the first trained neural network comprises:
a first plurality of convolutional hidden layers operating on the first image region;
a second plurality of convolutional hidden layers operating on the second image region; and
at least one fully connected hidden layer receiving output from both the first plurality of convolutional hidden layers and the second plurality of convolutional hidden layers, and outputting to an output layer of one or more nodes corresponding values each representing a probability of a post contrast phase; and present on the display device, output data based on the post contrast phase.

16. The system as recited in claim 15, wherein:
to obtain the first image region is performed using a second trained convolutional neural network with first input based on a set of one or more contiguous slices the 3D medial imagery;
to obtain the second image region is performed using a different third trained convolutional neural network with second input based on the set of one or more contiguous slices the 3D medial imagery.

17. The system as recited in claim 16, wherein execution of the one or more sequences of instructions further causes the one or more processors to determine the first set of one or more contiguous slices automatically on the processor using a different fourth trained convolutional neural network with first input based on the 3D medial imagery and output that indicates a probability that each slice includes the first anatomical feature.

18. The system as recited in claim 15, wherein the output data comprises an image of vascular density.

19. The system as recited in claim 15, wherein the output data comprises a set of output images displaced in the axial direction of vascular density.

20. The system as recited in claim 15, wherein the output data comprises a set of output images displaced in the axial direction of a tumor density or a tumor boundary.

21. The system as recited in claim 15, wherein the output data indicates a tumor density or a tumor boundary.

22. An apparatus configured as a trained neural network for measuring post contrast phase comprising:
a first plurality of convolutional hidden layers operating on a first image region that includes a first anatomical feature selected from a group consisting of an aorta, a portal vein, an inferior vena cava, a liver, a spleen and a renal cortex;
a second plurality of convolutional hidden layers operating on a different second image region that includes a different second anatomical feature selected from the group; and
at least one fully connected hidden layer receiving output from each of the first plurality of convolutional hidden layers and the second plurality of convolutional hidden layers and outputting to an output layer one or more nodes each representing a probability of a post contrast phase.

* * * * *